United States Patent
Wu et al.

(10) Patent No.: US 10,825,152 B2
(45) Date of Patent: Nov. 3, 2020

(54) DISTORTION MEASUREMENT AND CORRECTION FOR SPECTRALLY ENCODED ENDOSCOPY

(71) Applicant: CANON U.S.A., INC., Melville, NY (US)

(72) Inventors: Tzu-Yu Wu, Malden, MA (US); Bin Wu, West Roxbury, MA (US)

(73) Assignee: Canon U.S.A., Inc., Melville, NY (US)

(*) Notice: Subject to any disclaimer, the term of this patent is extended or adjusted under 35 U.S.C. 154(b) by 79 days.

(21) Appl. No.: 16/124,545

(22) Filed: Sep. 7, 2018

(65) Prior Publication Data

US 2019/0080439 A1    Mar. 14, 2019

Related U.S. Application Data

(60) Provisional application No. 62/558,691, filed on Sep. 14, 2017.

(51) Int. Cl.
  *G06T 5/50* (2006.01)
  *G06T 5/00* (2006.01)
  (Continued)

(52) U.S. Cl.
  CPC .......... *G06T 5/006* (2013.01); *A61B 1/00009* (2013.01); *G01J 3/2823* (2013.01);
  (Continued)

(58) Field of Classification Search
  CPC combination set(s) only.
  See application file for complete search history.

(56) References Cited

U.S. PATENT DOCUMENTS

| 3,976,360 A | 8/1976 | Schroder |
| 4,074,306 A | 2/1978 | Kakinuma et al. |

(Continued)

FOREIGN PATENT DOCUMENTS

| WO | 1999/044089 A1 | 9/1999 |
| WO | 2007/047690 A1 | 4/2007 |

(Continued)

OTHER PUBLICATIONS

Kang, D., et al., "Minature grating for spectrally-encoded endoscopy", Lab Chip, Feb. 25, 2013, pp. 1810-1816, vol. 13.

(Continued)

*Primary Examiner* — Omar S Ismail
(74) *Attorney, Agent, or Firm* — Canon U.S.A., Inc. I.P. Division

(57) ABSTRACT

Methods, apparatuses, systems, and storage mediums for correcting distortion of a spectrally encoded endoscopy (SEE) image are provided. A first reference pattern comprising a plurality of radial lines is scanned with an SEE spectral line to obtain a first image. Signs of a tangential shift and/or of a radial shift of the spectral line may be determined, and magnitudes of the tangential shift and of the radial shift may be computed. A second reference pattern comprising at least a circle with the SEE spectral line may be scanned to obtain a second image in a case where the radial shift is positive. The magnitude of the radial shift may be computed based on the magnitude of the tangential shift and a radius of the circle. The tangential shift and the radial shift may then be applied for correcting distortion.

18 Claims, 18 Drawing Sheets

(51) Int. Cl.
  *G01J 3/28*  (2006.01)
  *G01J 3/40*  (2006.01)
  *A61B 1/00*  (2006.01)

(52) U.S. Cl.
  CPC .............. *G01J 3/40* (2013.01); *G06T 5/50* (2013.01); *G01J 2003/283* (2013.01); *G06T 2207/10068* (2013.01)

(56) References Cited

U.S. PATENT DOCUMENTS

| | | | |
|---|---|---|---|
| 4,264,127 A | 4/1981 | Schumacher et al. | |
| 5,565,983 A | 10/1996 | Barnard | |
| 6,341,036 B1 | 1/2002 | Tearney et al. | |
| 6,485,413 B1 | 11/2002 | Boppart et al. | |
| 6,488,414 B1 | 12/2002 | Dawes et al. | |
| 6,522,403 B2 | 2/2003 | Wilson et al. | |
| 6,661,513 B1 | 12/2003 | Granger | |
| 6,831,781 B2 | 12/2004 | Tearney et al. | |
| 6,858,859 B2 | 2/2005 | Kusunose | |
| 7,003,196 B2 | 2/2006 | Ghiron et al. | |
| 7,158,234 B2 | 1/2007 | Uchiyama et al. | |
| 7,181,106 B2 | 2/2007 | Ushiro et al. | |
| 7,412,022 B2* | 8/2008 | Jupiter | G01N 23/046 250/363.06 |
| 7,447,408 B2 | 11/2008 | Bouma et al. | |
| 7,551,293 B2 | 6/2009 | Yelin et al. | |
| 7,796,270 B2 | 9/2010 | Yelin et al. | |
| 7,843,572 B2 | 11/2010 | Tearney et al. | |
| 7,859,679 B2 | 12/2010 | Bouma et al. | |
| 7,889,348 B2 | 2/2011 | Tearney et al. | |
| 7,894,058 B2 | 2/2011 | Wilson et al. | |
| 8,045,177 B2 | 10/2011 | Tearney et al. | |
| 8,114,012 B2 | 2/2012 | Fujita | |
| 8,141,260 B2 | 3/2012 | Pellen | |
| 8,145,018 B2 | 3/2012 | Shishkov et al. | |
| 8,203,708 B2 | 6/2012 | Lee et al. | |
| 8,289,522 B2 | 10/2012 | Tearney et al. | |
| 8,780,176 B2 | 7/2014 | Yelin | |
| 8,792,757 B2 | 7/2014 | Boudoux et al. | |
| 8,804,133 B2 | 8/2014 | Yelin et al. | |
| 8,812,087 B2 | 8/2014 | Yelin et al. | |
| 8,818,149 B2 | 8/2014 | Shishkov et al. | |
| 8,838,213 B2 | 9/2014 | Tearney et al. | |
| 8,987,649 B2 | 3/2015 | Jalali et al. | |
| 9,046,419 B2 | 6/2015 | Yelin et al. | |
| 9,090,315 B1 | 7/2015 | Stone et al. | |
| 9,192,515 B2 | 11/2015 | Papac et al. | |
| 9,254,089 B2 | 2/2016 | Tearney et al. | |
| 9,295,391 B1 | 3/2016 | Tearney et al. | |
| 9,360,542 B2 | 6/2016 | Reeder et al. | |
| 9,415,550 B2* | 8/2016 | Tearney | B29D 11/00769 |
| 9,438,897 B2 | 9/2016 | Barreto et al. | |
| 9,439,570 B2 | 9/2016 | Vertikov | |
| 9,557,154 B2 | 1/2017 | Tearney et al. | |
| 2002/0114566 A1 | 8/2002 | Fairchild et al. | |
| 2002/0145815 A1 | 10/2002 | Moriyama et al. | |
| 2003/0103189 A1* | 6/2003 | Neureuther | G01M 11/0264 351/159.74 |
| 2003/0142934 A1 | 7/2003 | Pan et al. | |
| 2004/0147810 A1 | 7/2004 | Mizuno | |
| 2005/0058352 A1* | 3/2005 | Deliwala | G01J 3/0229 382/232 |
| 2005/0155704 A1 | 7/2005 | Yokajty et al. | |
| 2006/0232846 A1* | 10/2006 | Himmer | G02B 26/0825 359/224.1 |
| 2007/0188855 A1 | 8/2007 | Shishkov et al. | |
| 2007/0233396 A1 | 10/2007 | Tearney et al. | |
| 2007/0276187 A1 | 11/2007 | Wiklof et al. | |
| 2008/0013960 A1 | 1/2008 | Tearney et al. | |
| 2008/0097225 A1 | 4/2008 | Tearney et al. | |
| 2008/0123927 A1* | 5/2008 | Miga | G06T 7/344 382/131 |
| 2009/0141360 A1 | 6/2009 | Koyama | |
| 2009/0153932 A1 | 6/2009 | Davis et al. | |
| 2010/0210937 A1 | 8/2010 | Tearney et al. | |
| 2010/0265380 A1* | 10/2010 | Fukuta | G02B 15/177 348/335 |
| 2011/0237892 A1 | 9/2011 | Tearney et al. | |
| 2011/0275899 A1 | 11/2011 | Tearney et al. | |
| 2012/0025099 A1 | 2/2012 | Yelin et al. | |
| 2012/0101374 A1 | 4/2012 | Tearney et al. | |
| 2012/0112094 A1 | 5/2012 | Kao et al. | |
| 2012/0328241 A1 | 12/2012 | Shishkov et al. | |
| 2013/0012771 A1 | 1/2013 | Robertson | |
| 2014/0071238 A1 | 3/2014 | Mertens et al. | |
| 2014/0125860 A1* | 5/2014 | Tofsted | H04N 5/238 348/349 |
| 2014/0285878 A1 | 9/2014 | Escuti et al. | |
| 2014/0378846 A1 | 12/2014 | Hosoda et al. | |
| 2015/0011896 A1 | 1/2015 | Yelin et al. | |
| 2015/0045622 A1 | 2/2015 | Shishkov et al. | |
| 2015/0105622 A1 | 4/2015 | Yelin et al. | |
| 2015/0131098 A1 | 5/2015 | Yang et al. | |
| 2015/0231841 A1 | 8/2015 | Tearney et al. | |
| 2015/0335248 A1 | 11/2015 | Huang et al. | |
| 2016/0320170 A1 | 11/2016 | Yun et al. | |
| 2016/0341951 A1 | 11/2016 | Tearney et al. | |
| 2016/0349417 A1 | 12/2016 | Tearney et al. | |
| 2017/0035281 A1* | 2/2017 | Takeuchi | G02B 23/26 |
| 2017/0111558 A1* | 4/2017 | Brueckner | G06T 7/80 |
| 2017/0167861 A1 | 6/2017 | Chen et al. | |
| 2017/0168232 A1 | 6/2017 | Tearney et al. | |
| 2017/0176736 A1 | 6/2017 | Yamamoto et al. | |
| 2017/0290492 A1 | 10/2017 | Hamm et al. | |
| 2017/0322079 A1 | 11/2017 | Do et al. | |
| 2018/0017778 A1 | 1/2018 | Ikuta et al. | |
| 2018/0120555 A1 | 5/2018 | Ikuta et al. | |
| 2018/0259318 A1* | 9/2018 | Yelin | G01N 15/1459 |

FOREIGN PATENT DOCUMENTS

| | | |
|---|---|---|
| WO | 2013/108209 A1 | 7/2013 |
| WO | 2014/031748 A1 | 2/2014 |
| WO | 2014/104405 A1 | 7/2014 |
| WO | 2015/116939 A1 | 8/2015 |
| WO | 2015/116951 A2 | 8/2015 |
| WO | 2015/116974 A1 | 8/2015 |
| WO | 2017/024145 A1 | 2/2017 |
| WO | 2017/117203 A1 | 7/2017 |
| WO | 2017/139657 A1 | 8/2017 |
| WO | 2017/165511 A1 | 9/2017 |

OTHER PUBLICATIONS

Kang, D., et al., "Spectrally-encoded color imaging", Optics Express, Aug. 17, 2009, pp. 15239-15247, vol. 17, No. 17.

Moharam, M.G., et al., "Formulation for stable and efficient implementation of the rigorous coupled-wave analysis of binary gratings", J. Opt. Soc. Am. A, May 1995, pp. 1068-1076, vol. 12, No. 5.

Pitris, C., et al., "A GRISM-based probe for spectrally encoded confocal microscopy", Optics Express, Jan. 27, 2003, pp. 120-124, vol. 11, No. 2.

Wu, J., et al., "Paired-angle-rotation scanning optical coherence tomography forward-imaging probe", Optics Letters, vol. 31, No. 9, May 1, 2006.

Yun, S.H., et al., "High-speed spectral-domain optical coherence tomography at 1.3 µm wavelength", Opt Express, Dec. 29, 2003, pp. 3598-3604, vol. 11, No. 26 (ten page PDF submitted).

Zeidan, Adel, et al., "Miniature forward-viewing spectrally encoded endoscopic probe", Optics Letters, Aug. 15, 2014, pp. 4871-4874, vol. 39, No. 16.

Tearney, G. J., et al., "Spectrally encoded miniature endoscopy", Optics Letters, vol. 27, No. 6, Mar. 15, 2002.

Yelin, D., et al., "Three-dimensional miniature endoscopy", Nature, Oct. 19, 2006, pp. 765, vol. 443.

Adel Zeidan, et al., "Spectral imaging using forward-viewing spectrally encoded endoscopy", Biomed Opt Express. Feb. 1, 2016, No. 7, vol. 2, pp. 392-398, Published online Jan. 8, 2016, doi: 10.1364/

(56) References Cited

OTHER PUBLICATIONS

BOE.7.000392, https://www.ncbi.nlm.nih.gov/pmc/articles/PMC4771457/ (seven page PDF submitted).

Frederic Devernay, et al., "Automatic calibration and removal of distortion from scenes of structured environments", HAL Id: hal-00821474, https://hal.inria.fr/hal-00821474, Submitted on May 10, 2013, https://hal.archives-ouvertes.fr/hal-00821474/document (twelve page PDF submitted).

* cited by examiner

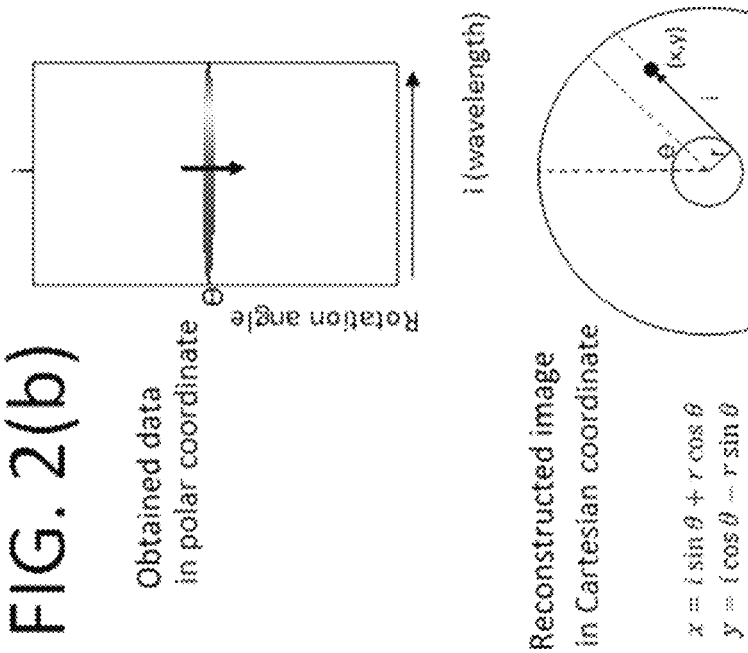
FIG. 2(b) Obtained data in polar coordinate
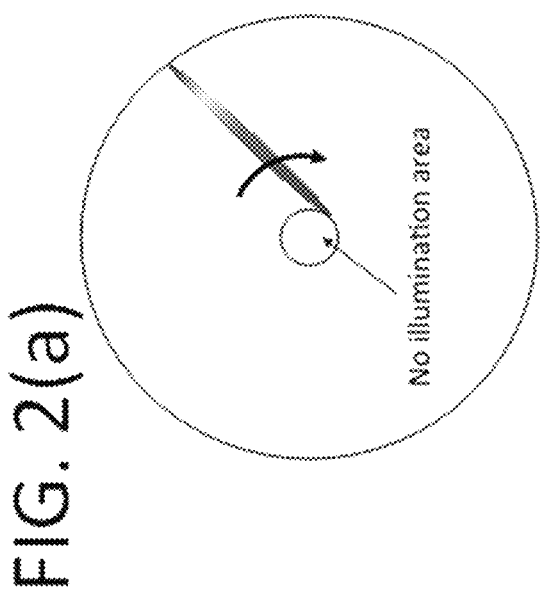
FIG. 2(c) Reconstructed image in Cartesian coordinate
Equation 1: $x = l \sin\theta + r \cos\theta$
$y = l \cos\theta - r \sin\theta$
FIG. 2(a)

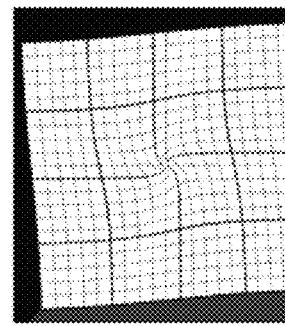 FIG. 4(a-1)
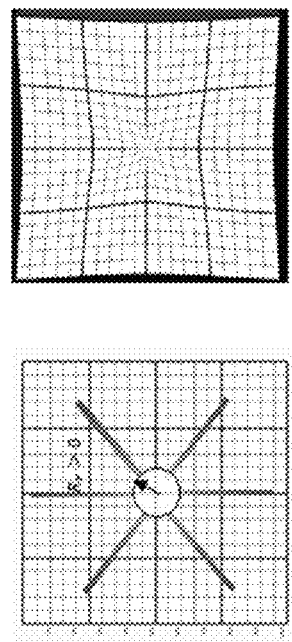 FIG. 4(a-2)
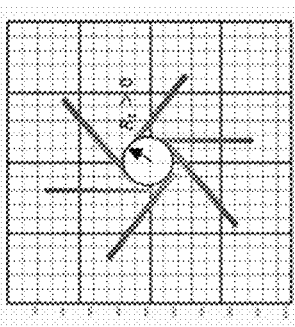 FIG. 4(b-1) FIG. 4(b-2)
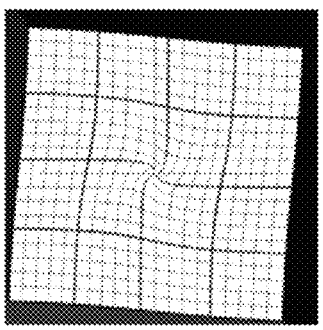 FIG. 4(c-2)
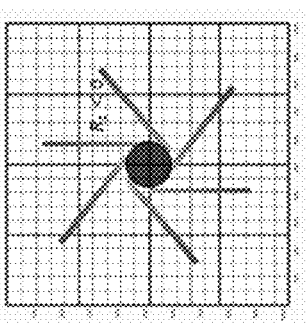 FIG. 4(c-1)
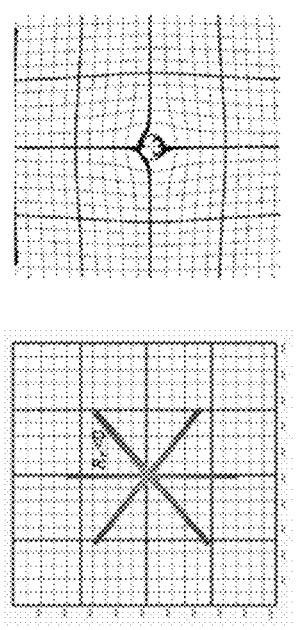 FIG. 4(d-1) FIG. 4(d-2)

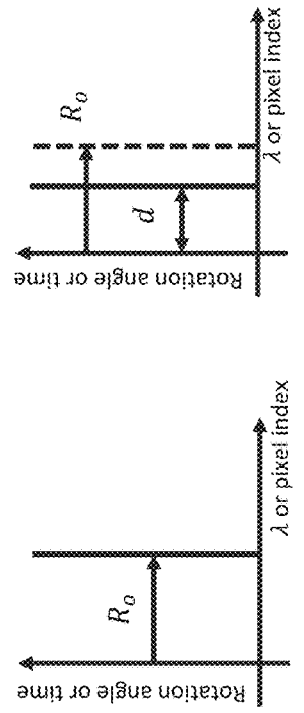
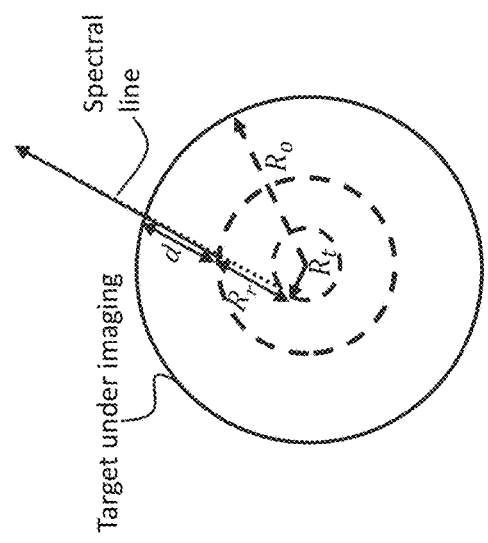
FIG. 10(a)   FIG. 10(b)   FIG. 10(c)
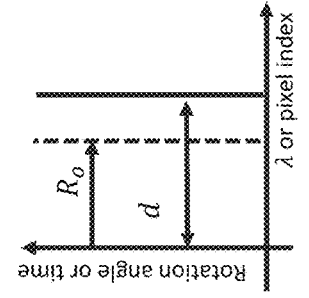
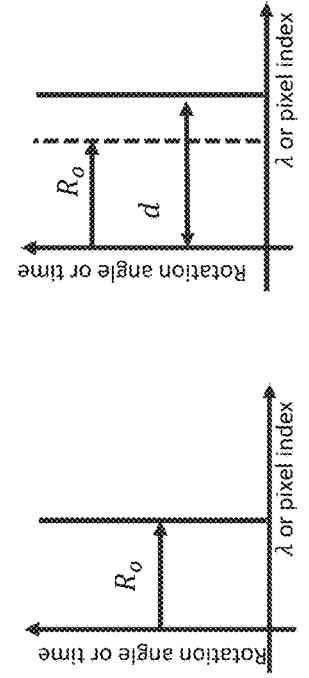
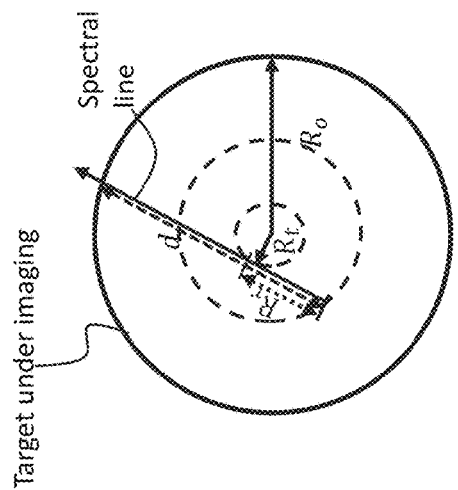
FIG. 11(a)   FIG. 11(b)   FIG. 11(c)

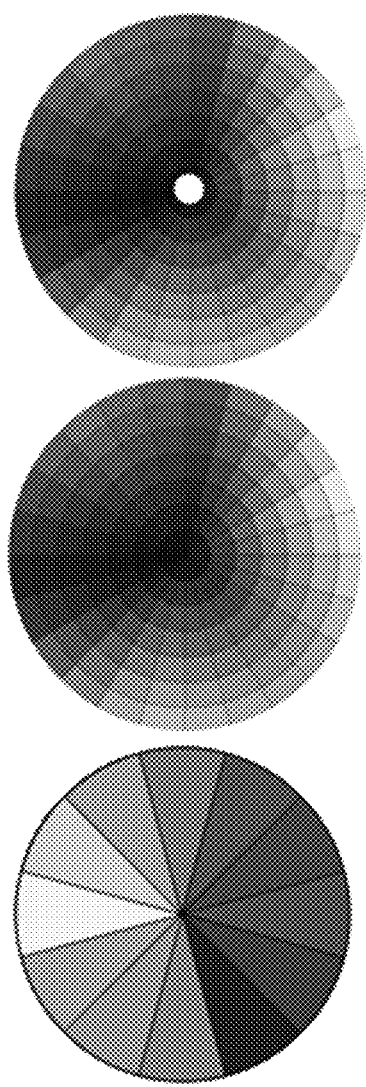
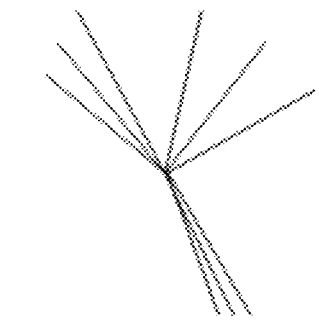
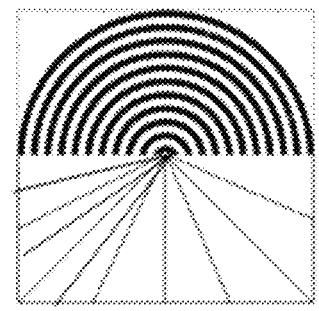
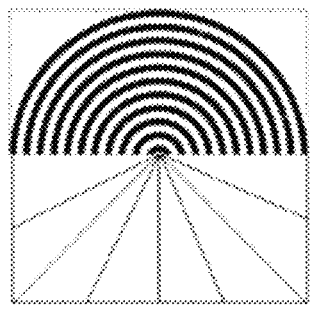
FIG. 18(a) FIG. 18(b) FIG. 18(c) FIG. 18(d) FIG. 18(e) FIG. 18(f)

DISTORTION MEASUREMENT AND CORRECTION FOR SPECTRALLY ENCODED ENDOSCOPY

CROSS-REFERENCE TO RELATED APPLICATIONS

This application relates, and claims priority, to U.S. Patent Application Ser. No. 62/558,691, filed Sep. 14, 2017, the entire disclosure of which is incorporated by reference herein in its entirety.

BACKGROUND

Field of the Disclosure

The present disclosure relates in general to one or more embodiments of a spectrally encoded endoscope (SEE), and more particularly, to distortion measurement and correction of image data acquired by the one or more embodiments of the spectrally encoded endoscope, including, but not limited to, miniature endoscopes, ultra-miniature endoscopes, etc.

Description of the Related Art

Spectrally encoded endoscopy (SEE) is a technology that utilizes optical fibers, miniature optics, and a diffraction grating for high-speed imaging through small diameter and flexible endoscopic probes. The polychromatic light emanating from the SEE probe is spectrally dispersed and projected in such a way that each color (wavelength) illuminates a different location on a target, such as a tissue, along a line (the dispersive line). Reflected light from the tissue can be collected and decoded by a spectrometer to form a line of image, with each pixel of the line image corresponding to the specific wavelength of illumination. Spatial information in the other dimension perpendicular to the dispersive line is obtained by moving the probe using a motor or a galvanometric motor. For the forward viewing SEE imaging, spatial information in the other dimension perpendicular to the dispersive line is obtained by rotating the probe using a rotary motor such that the target is circularly scanned.

Due to the fabrication and assembly issues of SEE probes, the scanning spectral line is often shifted from the designed position on the imaging object causing distortion image. The distorted image may appear as or similarly to the images shown in FIG. 1. Currently, there has not been an efficient method to resolve the distortion issues. Accordingly, it would be desirable to provide one or more SEE techniques for use in at least one optical device, assembly or system to achieve efficient resolution of distortion, including any method to efficiently correct distortion in real time.

SUMMARY

At least one embodiment of a method for correcting distortion of a spectrally encoded endoscopy (SEE) image is provided herein. A first reference pattern comprising a plurality of radial lines may be scanned with an SEE spectral line to obtain a first image. A sign of a tangential shift of the spectral line may be determined based on a slope of at least one of the radial lines of the first image in a polar coordinate. A magnitude of the tangential shift may be computed based on at least one of the radial lines of the first image in either a polar coordinate or a Cartesian coordinate. A sign of a radial shift of the spectral line may be determined based on whether the slope has a turning point or not. A magnitude of the radial shift may be determined by measuring a location of the turning point in a case where the radial shift is determined to be negative. A second reference pattern comprising at least a circle is scanned to obtain a second image in a case where the radial shift is determined to be positive. The magnitude of the radial shift is computed based on the magnitude of the tangential shift and a radius of the circle. The tangential shift and the radial shift are then applied for correcting distortion.

In one embodiment, the step of computing the magnitude of the tangential shift comprises determining a shift of the radial line of the first image from an original position in the Cartesian coordinate. Alternatively, the step of computing the magnitude of the tangential shift may comprise selecting at least three radial lines with the spectral line that are equally spaced from each other with an angle and each intersecting with the spectral line at an intersection point and computing the magnitude of the tangential shift based on the angle, a first distance between the intersecting points of a first and a second of the at least three radial lines, and a second distance between the intersecting points of the second and a third of the intersecting points.

The step of computing a magnitude of the radial shift may further comprise measuring the location of the turning point by determining where a second derivative of the radial line is zero in a case where the radial shift is determined to be negative. In one or more embodiments, when the sign of the radius shift is positive, the magnitude of the radial shift may be computed by geometric relations or by relationship(s) using the following equation:

$$R_r = \sqrt{R_0^2 - R_t^2} - d$$

where $R_r$ is the radial shift, $R_t$ is the tangential shift, $R_0$ is the radius of the circle, and d is the distance between the circle and a target radius. When the sign of the radius shift is negative, the magnitude of the radial shift may be computed by the relations using the following equation:

$$R_r = d - \sqrt{R_0^2 - R_t^2}$$

where $R_r$ is the radial shift, $R_t$ is the tangential shift, $R_0$ is the radius of the circle, and d is the distance between the circle and a target radius. One or more methods may decompose an SEE image distortion into orthogonal tangential and radial distortions, quantitatively measure the orthogonal spectral line shifts, and correct the distortions in real time (e.g., in software and/or hardware in real time). One or more embodiments may involve calibration procedure(s) to measure an amount of distortion and decompose the distortion into tangential and radial distortions. One or more embodiments may use the measured orthogonal distortion data to correct both the tangential and radial distortions (e.g., in software and/or hardware in real time). An SEE image may be represented in either Cartesian coordinate(s) or polar coordinate(s). Raw image data may be collected in the polar coordinate in which a horizontal axis represents a wavelength of the spectral line or pixel index of a line sensor built in spectrometer, and a vertical axis represents the rotation angle of the spectral line or the time when the spectral line is obtained.

In one or more embodiments, the step of applying the tangential shift and the radial shift for correcting distortion further comprises applying the tangential shift and the radial shift to determine actual location (x', y') of the radial lines represented by:

$$x' = \rho \cos \theta - R_t \sin \theta + R_r \cos \theta$$

$$y' = \rho \sin \theta + R_t \cos \theta + R_r \sin \theta$$

where ρ is pixel index along the SEE spectral line, and θ is rotation angle of the SEE spectral line.

In another embodiment, a method for correcting distortion of a spectrally encoded endoscopy (SEE) image comprising following steps is provided herein. A first reference pattern comprising a plurality of radial lines is scanned with an SEE spectral line to obtain a first image. A sign of a tangential shift of the spectral line is determined based on a slope of at least one of the radial lines of the first image in a polar coordinate. A second reference pattern comprising at least two concentric circles is scanned with the SEE spectral line to obtain a second image, the two concentric circles having a first radius and a second radius, respectively. The magnitude of the tangential shift and a magnitude of a radial shift of the spectral line are scanned by measuring locations of the spectral line corresponding to the two concentric circles in the polar coordinate. The tangential shift and the radial shift are applied for correcting distortion. The step of computing the magnitude of the tangential shift may comprise determining a shift of the radial line of the first image from an original position in the Cartesian coordinate. The radial shift may be calculated based on the relationship:

$$R_r = \frac{R_2^2 - R_1^2}{2(d_2 - d_1)} - \frac{d_1 + d_2}{2},$$

and the tangential shift may be calculated based on the relationship:

$$R_t^2 = \frac{R_2^2 + R_1^2}{2} - \frac{(R_2^2 - R_1^2)^2}{4(d_2 - d_1)^2} - \frac{(d_2 - d_1)^2}{4}.$$

The step of applying the tangential shift and the radial shift for correcting distortion further comprises applying the tangential shift and the radial shift to determine actual location (x', y') of the radial lines represented by:

$x' = \rho \cos\theta - R_t \sin\theta + R_r \cos\theta$ $y' = \rho \sin\theta + R_t \cos\theta + R_r \sin\theta,$ where ρ is pixel index along the SEE spectral line, and θ is rotation angle of the SEE spectral line.

In another embodiment, a first reference pattern comprising a plurality of radial lines is scanned with an SEE spectral line to obtain a first image. A sign of a tangential shift of the spectral line is determined based on a slope of at least one of the radial lines of the first image in a polar coordinate. A magnitude of the tangential shift is determined based on a shift of at least one of the plurality of the radial lines on a Cartesian coordinate or based on at least three angularly equally radial lines included in the plurality of radial lines scanned by the SEE spectral line. The magnitude of the tangential shift is computed based on the shift of at least one of the radial lines or based on at least three angularly equally spaced radial lines included in the plurality of radial lines. A second reference pattern comprising at least two concentric circles is scanned with the SEE spectral line to obtain a second image, the two concentric circles having a first radius and a second radius, respectively. A ratio of the second radius to the first radius is provided. A radial shift of the spectral lines is computed based on the tangential shift and the ratio, and the tangential shift and the radial shift are applied for correcting distortion.

In one or more embodiments, the step of computing the magnitude of the tangential shift may comprise determining a shift of the radial line of the first image from an original position in the Cartesian coordinate. The step of computing the magnitude of the tangential shift may also comprise selecting at least three radial lines that are equally spaced from each other with an angle and each intersecting with the spectral line at an intersection point and computing the magnitude of the tangential shift based on the angle, a first distance between the intersecting points of a first and a second of the at least three radial lines, and a second distance between the intersecting points of the second and a third of the intersecting points.

The radial shift may be calculated based on the relationship of:

$$R_r = \frac{-(d_1 \times k^2 - d_2) \pm \sqrt{k^2 \times (d_2 - d_1)^2 - R_t^2(k^2 - 1)^2}}{k^2 - 1}$$

where k is the ratio of the second radius to the first radius. The step of applying the tangential shift and the radial shift for correcting distortion further comprises, in one or more embodiments, applying the tangential shift and the radial shift to determine actual location (x', y') of the radial lines represented by:

$x' = \rho \cos\theta - R_t \sin\theta + R_r \cos\theta$ $y' = \rho \sin\theta + R_t \cos\theta + R_r \sin\theta$ where ρ is pixel index along the SEE spectral line, and θ is rotation angle of the SEE spectral line.

In another embodiment, a method for correcting distortion of a spectrally encoded endoscopy (SEE) image is provided herein. A first reference pattern comprising a plurality of radial lines is scanned with an SEE spectral line to obtain a first image. A sign of a tangential shift of the spectral line is determined based on a slope of at least one of the radial lines of the first image in a polar coordinate. A magnitude of the tangential shift is determined based on a shift of at least one of the plurality of the radial lines on a Cartesian coordinate or based on at least three angularly equally radial lines included in the plurality of radial lines scanned by the SEE spectral line. A second reference pattern comprising at least two concentric circles is scanned with the SEE spectral line to obtain a second image, the two concentric circles having a first radius and a second radius, respectively. A ratio of the second radius to the first radius is provided. Two possible values of the magnitude of a radial shift of the spectral lines may be computed based on the tangential shift and the ratio. One of the possible values is selected to calculate pixel coordinate(s) of the radial lines imaged by the spectral line. The tangential shift and the radial shift are applied for correcting distortion. The other of the possible values of the magnitude of the radial shift is selected in a case where the distortion is not corrected by the first possible value.

According to other aspects of the present disclosure, one or more additional devices, one or more systems, one or more methods and one or more storage mediums using, or for use with, one or more SEE distortion correction techniques are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 2(a) shows at least one embodiment of a tangentially shifted spectral line scanning in a target plane in accordance with one or more aspects of the present disclosure;

FIG. 2(b) shows at least one embodiment of an image of the scanning pattern presented in a polar coordinate in accordance with one or more aspects of the present disclosure;

FIG. 2(c) shows at least one embodiment of an image of the scanning pattern that also may be reconstructed in Cartesian coordinate in accordance with one or more aspects of the present disclosure;

FIGS. 4(a-1) and 4(a-2) show at least one embodiment of the scanning pattern on a grid object with an outward radial shift (where $R_r>0$) and the simulated distortion due to the outward radial shift, respectively, in accordance with one or more aspects of the present disclosure;

FIGS. 4(b-1) and 4(b-2) show the scanning pattern on a grid object with an inward radial shift (where $R_r<0$) and the simulated image distorted due to the inward radial shift, respectively, in accordance with one or more aspects of the present disclosure;

FIGS. 4(c-1) and 4(c-2) show at least one embodiment of the scanning pattern on a grid object with a positive tangential shift (where $R_t>0$) and the simulated distortion due to the tangential shift, respectively, in accordance with one or more aspects of the present disclosure;

FIGS. 4(d-1) and 4(d-2) show at least one embodiment of the scanning pattern on a grid object with a negative tangential shift (where $R_t<0$) and the simulated distortion due to the negative tangential shift, respectively, in accordance with one or more aspects of the present disclosure;

FIGS. 10(a) to 10(c) show at least one embodiment of a reference pattern (see circular pattern with radius of $R_o$ being scanned by the SEE spectral line in FIG. 10(a)), an undistorted image in polar coordinate (see FIG. 10(b) where $R_r=0$ and $R_t=0$), and a distorted image in polar coordinate (see FIG. 10(c) where $R_r>0$ and $R_t>0$) for at least one embodiment of a method for determining $R_r$ using a circular pattern in accordance with one or more aspects of the present disclosure;

FIGS. 11(a) to 11(c) show at least one embodiment of a circular pattern (see circular pattern with radius of $R_o$ being scanned by the SEE spectral line in FIG. 11(a)) scanned by the SEE spectral line, an undistorted image in polar coordinate (see FIG. 11(b) where $R_r=0$ and $R_t=0$), and a distorted image in polar coordinate (see FIG. 11(c) where $R_r<0$ and $R_t>0$) for at least one embodiment of the method for determining $R_r$ using circular pattern when $R_r<0$ in accordance with one or more aspects of the present disclosure;

FIGS. 18(*a*)-18(*f*) illustrate embodiment examples of patterns for different calibration purposes in accordance with one or more aspects of the present disclosure;

DETAILED DESCRIPTION

Figure 1:
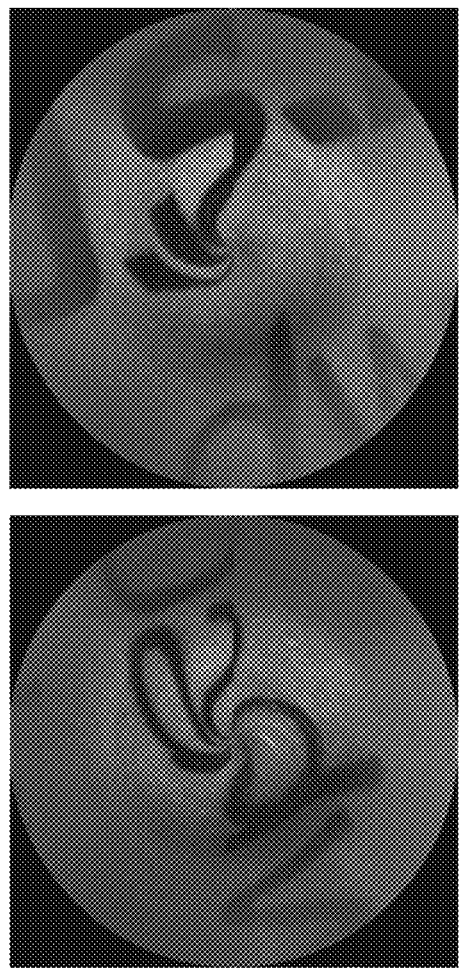
FIG. 1 shows examples of SEE forward view images in accordance with one or more aspects of the present disclosure.

The following description is of certain illustrative embodiments, although other embodiments may include alternatives, equivalents, and modifications. Additionally, the illustrative embodiments may include several novel features, and a particular feature may not be essential to practice one or more embodiments of the devices, systems, and methods described herein. Embodiments will be described below with reference to the attached drawings. Like numbers refer to like elements throughout. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an endoscope as disclosed in the following which is used to inspect an inside a human body may also be used to inspect other objects. Examples of specialized endoscopes which are examples of endoscope in which an embodiment may be implemented including: angioscope; anoscope; arthroscope; arterioscope; arthroscope, bronchoscope; capsule endoscope; choledochoscope; colonoscope; colposcope; cystoscope; encephaloscope; esophagogastroduodenoscope; esophagoscope; gastroscope; hysteroscope; laparoscope; laryngoscope; mediastinoscope; nephroscope; neuroendoscope; proctoscope; resectoscope; rhinoscope; sigmoidoscope; sinusoscope; thoracoscope; ureteroscope; uteroscope; borescope; fiberscope; inspection camera; and any specialized endoscope which may be adapted to include an embodiment. The endoscope may be flexible or rigid. An embodiment may also be a probe or an imaging apparatus.

One or more devices, optical systems, methods, and storage mediums for correcting distortion(s) in an image, such as an SEE image, are disclosed herein. In accordance with at least one aspect of the present disclosure, one or more devices, optical systems, methods, and storage mediums discussed herein use a distortion correction technique to provide a direct image/view or a forward image/view.

One method of speeding up the gathering of information is to encode a component of the spatial information with spectral information. In the context of endoscopy, one example that may be used is referred to as spectrally encoded endoscopy (SEE), which uses the wavelength of the illumination light to encode spatial information from a sample. Such SEE endoscope technology increases the speed with which images may be obtained and improves the efficiency of performing diagnosis and treatment through smaller diameter endoscopic probes and/or smaller or minimized needles. SEE is an endoscope technology which uses a broadband light source, a rotating grating and a spectroscopic detector to encode spatial information on a sample. When illuminating light to the sample, an object and/or a patient (or a portion thereof), the light is spectrally dispersed along one illumination line, such that the dispersed light illuminates a specific position of the illumination line with a specific wavelength. When the reflected light from the sample is detected with the spectrometer, the intensity distribution is analyzed as the reflectance along the line. By rotating or swinging the grating back and forth to scan the illumination line, a two-dimensional image of the sample is obtained.

SEE is a technology that may utilize optical fibers, miniature optics, and a diffraction grating (or prism) for high-speed imaging through small diameter and flexible endoscopic probes. Polychromatic light emanating from the SEE probe is spectrally dispersed and projected in such a way that that each color (wavelength) illuminates a different location on the sample in one line (the dispersive line, spectral line, or illumination line). Reflected (or scattered) light from the sample may be collected and decoded by a spectrometer and/or a detector to form an image line. Each position of the line corresponds with a specific wavelength of the illumination light. Spatial information in another dimension substantially perpendicular to the dispersive line may be obtained by moving the probe. SEE has been used to produce high quality images in two and three dimensions as well as in color. SEE may be accomplished by using a broad bandwidth light input into a single optical fiber. By rotating or swinging the grating back and forth to scan an illumination line along which the light is spectrally dispersed, a two-dimensional image of the sample is obtained.

Figures 3A, 3B, 3C:
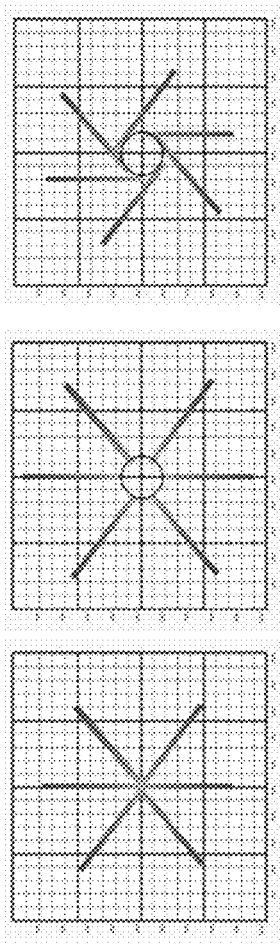
FIG. 3(a) shows at least one embodiment of a designed scanning pattern of or on an object in accordance with one or more aspects of the present disclosure.
FIG. 3(b) shows at least one embodiment of the scanning pattern shifted along a spectral direction, such as a spectral line direction, in accordance with one or more aspects of the present disclosure.
FIG. 3(c) shows at least one embodiment of the scanning pattern shifted along a scanning direction in accordance with one or more aspects of the present disclosure.

FIG. 1 shows examples of SEE forward view images. As discussed above, distortion of images obtained by at least one embodiment of an SEE apparatus often occurs when the scanning spectral line is shifted due to fabrication and/or assembly issues. The distortion in the SEE forward view image is the combination of distortions caused by at least two shifts, including a radial shift and a tangential shift, which present the shift along the spectral line direction and the shift along the scanning direction, respectively. FIG. 2(*a*) shows at least one embodiment of a tangentially shifted spectral line scanning in a target plane. As shown in FIG. 2(*a*), the shift of the scanning spectral line results in a no-illumination area in a central portion of the target plane. The image of the scanning pattern may be presented in a polar coordinate as shown in FIG. 2(*b*). The image of the scanning pattern may also be reconstructed in Cartesian coordinate as shown in FIG. 2(*c*). FIG. 3(*a*) shows at least one embodiment of a designed scanning pattern of an object. FIG. 3(b) shows the scanning pattern with the radial shift and FIG. 3(c) shows the scanning pattern with the tangential shift. As shown in FIG. 2(c), the image with only tangential shift may be reconstructed by the equation (1) as:

$$x = i\sin\theta + r\cos\theta$$

$$y = i\cos\theta + r\sin\theta \quad (1)$$

To quantify the total amount of distortion and to further correct the distortion, the spectral line shifts may be measured as distortion measurement metrics. FIG. 4 shows the distortion effects of the spectral line shift separated into two orthogonal directions, including radial shift $R_r$ and tangential shift $R_t$. FIG. 4(a)-1 shows the at least one embodiment of the scanning pattern on a grid object with an outward radial shift, that is, $R_r>0$. The distortion of the image caused by the outward radial shift of the spectral line presented in FIG. 4(a)-1 may be simulated as shown in FIG. 4(a)-2. FIG. 4(b)-1 shows the at least one embodiment of the scanning pattern on a grid object with an inward radial shift, that is, $R_r<0$, and FIG. 4(b)-2 shows the simulated distortion caused by the inward radial shift of the spectral line. FIG. 4(c)-1 shows the at least one embodiment of the scanning pattern of a spectral line on a grid object with a positive tangential shift, $R_t>0$, and FIG. 4(c)-2 shows the simulated distortion caused by the positive tangential shift. FIG. 4(d)-1 shows the at least one embodiment of the scanning pattern of a spectral line on a grid object with a negative tangential shift $R_t<0$, and FIG. 4(d)-2 shows the simulated distortion as a result of the negative tangential shift.

Figure 5:
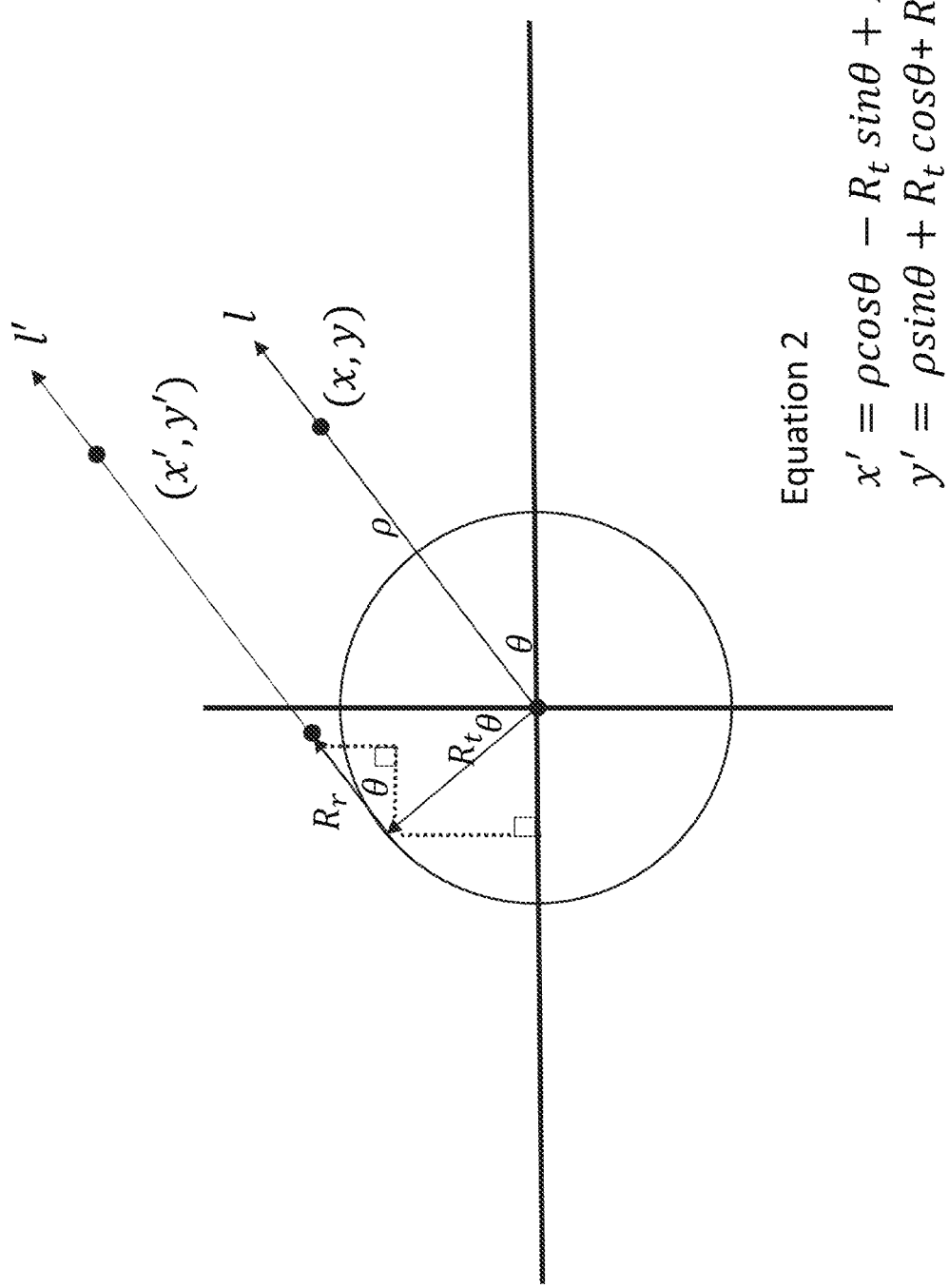
FIG. 5 shows at least one embodiment of a coordinate of a scanning spectral line in accordance with one or more aspects of the present disclosure.

FIG. 5 shows a coordinate of the scanning spectral line, where:

l presents the desired spectral line, l' presents the shifted spectral line, $R_r$ is the radial shift of the spectral line, $R_t$ is the tangential shift of the spectral line, ($\rho$, $\theta$) is the polar coordinate of the pixel of interested in the desired spectral line, where $\rho$ is pixel index along the spectral line and $\theta$ is the rotation angle of the spectral line, (x, y) is the pixel target imaged in the desired image, and (x', y') is the target pixel actually imaged in the resulted or resulting image due to distortion.

With the measured $R_r$ and $R_t$, the pixel location may be computed using equations (2) and (3) and placed at the actual location (x', y') instead of being located at the location (x, y).

$$x' = \rho\cos\theta - R_t\sin\theta + R_r\cos\theta \quad (2)$$

$$y' = \rho\sin\theta + R_t\cos\theta + R_r\sin\theta \quad (3)$$

As the actual location (x', y') may be correctly computed, the distortion in the image may be corrected. The tangential shift $R_t$ and the radial shift $R_r$ may be either positive or negative. The spectral line as shown in FIG. 5 and the equations (2) and (3) present the situation where $R_t>0$ and $R_r>0$. It will be appreciated that these equations are also applicable for the distortion caused by negative shifts, that is, $R_t<0$ and $R_r<0$.

Figure 6A:
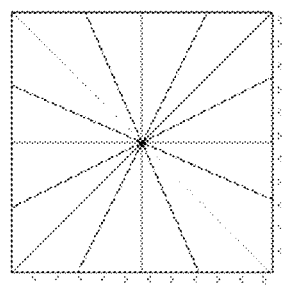
FIGS. 6(a) to 6(f) show at least one embodiment of an original imaging target (see FIGS. 6(a) and 6(d)) and the simulated distorted image in both polar and Cartesian coordinates (see FIGS. 6(b)-6(c) where $R_t>0$ and see FIGS. 6(e)-6(f) where $R_t<0$) allowing a user to determine the sign of the tangential shift $R_t$ in accordance with one or more aspects of the present disclosure.
Figure 6B:
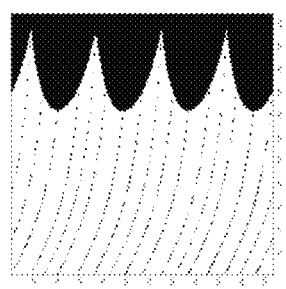
Figure 6C:
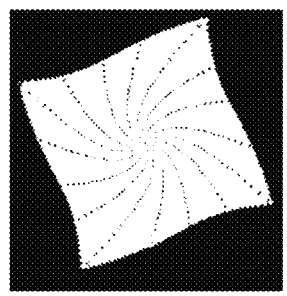
Figure 6D:
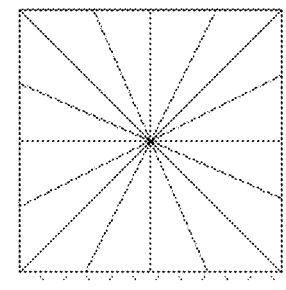
Figure 6E:
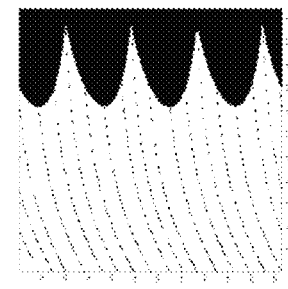
Figure 6F:
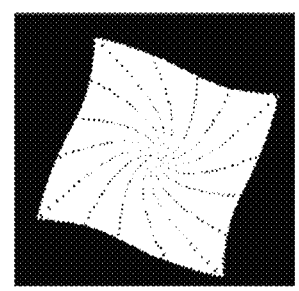

To appropriately apply equations (2) and (3) for distortion correction, in one or more embodiments, not only the magnitude ($|R_t|$ and $|R_r|$), but also the signs of the spectral shifts $R_t$ and $R_r$ have to be determined. To identify the sign of the tangential shift $R_t$, an original imaging target in the form of a grid, for example, the target planes as shown in FIGS. 4(a)-(d) may be provided. In one or more embodiments, the sign of $R_t$ may be identified by the orientation of a rotation pattern in a distorted image in a Cartesian coordinate (examples may be seen in FIG. 4(c)-2 and FIG. 4(d)-2 where the original imaging target is a grid). In one or more embodiments, the sign of $R_t$ may be identified from a raw data set in a polar coordinate (e.g., FIG. 1B) which may be beneficial for computing speed. Alternatively, a target plane with multiple radial lines as shown in FIG. 6(a) may be provided to perform the scanning. FIG. 6 shows an example of imaging a radial line to determine the sign of $R_t$ by identifying the sign of the slope of the lines in a polar image. FIG. 6(b) shows the simulated image in a polar coordinate. When the radial line image is not distorted, that is, when $R_t=0$, the lines in the polar coordinate have slope=0. Due to distortion, the slope of the radial lines in a polar coordinate may change. FIG. 6(b) shows the simulated image in a polar coordinate with negative slope which is distorted caused by a positive tangential shift ($R_t>0$). FIG. 6(c) shows the simulated image in a Cartesian coordinate with the positive tangential shift. FIG. 6(d) shows the same radial lines of the target plane, while FIGS. 6(e) and 6(f) show the simulated distorted image with $R_t<0$ in a polar coordinate and a Cartesian coordinate, respectively, in at least one embodiment. FIG. 6(e) shows the simulated image in a polar coordinate with positive slope, which is distorted due to the negative $R_t$ shift.

Figure 7A:
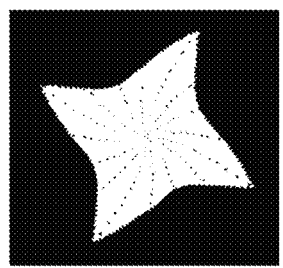
FIGS. 7(a) to 7(c) show at least one embodiment of an original imaging target (see FIG. 7(a)) and the distorted images in both the polar coordinate and the Cartesian coordinate (see FIGS. 7(b)-7(c), respectively) while $R_r>0$ and $R_t>0$ in accordance with one or more aspects of the present disclosure.
Figure 7B:
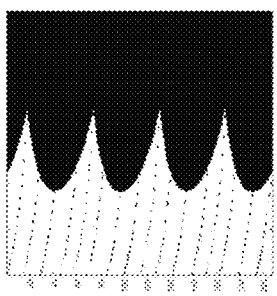
Figure 7C:
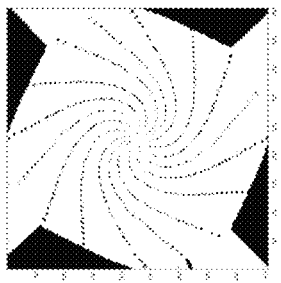
Figure 7D:
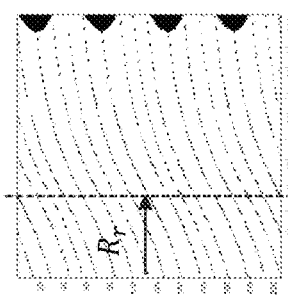
FIGS. 7(d) to 7(f) show at least one embodiment of the original imaging target (see FIG. 7(d)) and the simulated images in the polar coordinate and the Cartesian coordinate (see FIGS. 7(e)-7(f), respectively) with $R_r<0$ and $R_t<0$ in accordance with one or more aspects of the present disclosure.
Figure 7E:
Figure 7F:
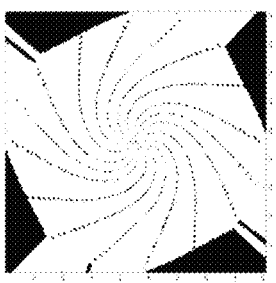
Figure 7G:
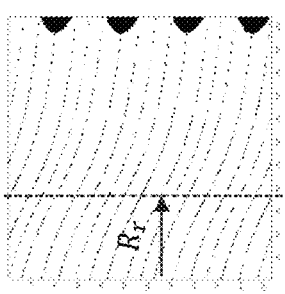
FIGS. 7(g) to 7(i) show at least one embodiment of the original imaging target (see FIG. 7(g)) and the simulated images in both the polar coordinate and the Cartesian coordinate (see FIGS. 7(h)-7(i), respectively) with $R_r<0$ and $R_t>0$ in accordance with one or more aspects of the present disclosure.
Figure 7H:
Figure 7I:

The radial line pattern as shown in FIG. 6(a) is not affected by the radial spectral line shift $R_r$ in Cartesian coordinate, in one or more embodiments, but is determined by the tangential spectral line shift $R_t$. However, the distortion in radial line pattern caused by a radial spectral line shift may cause noticeable change in the slope of the radial lines in the polar coordinate. FIG. 7 shows the simulated images with distortion caused by both the radial shift and tangential shift of the spectral line. As shown in FIGS. 7(a) to 7(c), both of the radial shift $R_r$ and the tangential shift $R_t$ are positive ($R_r>0$ and $R_t>0$). FIGS. 7(d) to 7(f) shows the simulated images with negative radial shift ($R_r<0$) and negative tangential shift ($R_t<0$). FIGS. 7(g) to 7(i) shows the simulated images with negative radial shift ($R_r<0$) and positive tangential shift ($R_t>0$). As observed from FIGS. 7(a) to 7(i), if $R_r<0$, there is a slope transition point in the image in the polar coordinate where the second derivative of the lines is equal to zero as shown in FIGS. 7(e) and 7(h). The magnitude of $R_r$ can be determined by measuring the location (pixel index) of the transition point that occurs at the position with largest slope, that is, where the second derivatives of the line is zero. However, when $R_r>0$, such transition point does not exist as shown in FIG. 7(b) regardless whether the tangential $R_t$ is positive or negative. Therefore, the sign of the radial shift $R_r$ may be determined by imaging a reference target with a radial line pattern and by observing the slope transition point of the radial lines in the polar coordinate. In a case where the second derivative of the lines in the polar coordinate changes the sign of the radial shift, $R_r$ is negative; otherwise, $R_r$ is positive.

Figure 8A:
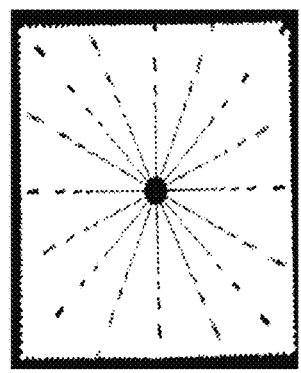
FIGS. 8(a) to 8(c) show at least one embodiment of a reference radial line pattern (FIG. 8(a)), a simulated distortion image (FIG. 8(b)), and a restored image (FIG. 8(c)) for at least one embodiment of a method for measuring the magnitude of $R_t$ in Cartesian coordinate in accordance with one or more aspects of the present disclosure.
Figure 8B:
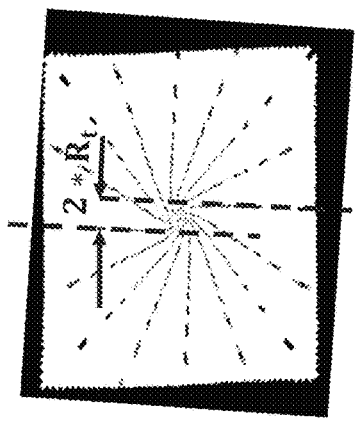
Figure 8C:
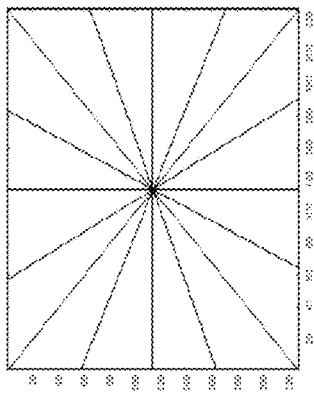

In at least one embodiment, $R_t$ may be obtained by measuring the radial line shift in a distorted image in a Cartesian coordinate. The radial line pattern as shown in FIG. 8(a) is not distorted by the radial shift $R_r$ in the Cartesian coordinate. The distortion manifested in the radial line image may be used to measure the magnitude of tangential shift $|R_t|$ regardless of the presence of $R_r$. FIG. 8(b) shows the distorted image with the radial lines shifted from its original position with the amount of $|R_t|$. FIG. 8(c) shows the image restored by applying the measure $R_t$ to equations (2) and (3). The radius of the central hole in FIG. 8(c) is equal to $R_t$. That is, in one embodiment, the magnitude of the tangential shift $|R_t|$ may be determined from the shift of the radial line from its original position in the Cartesian coordinate, that is, the shift from the original position as shown in FIG. 8(a).

Figure 9C:
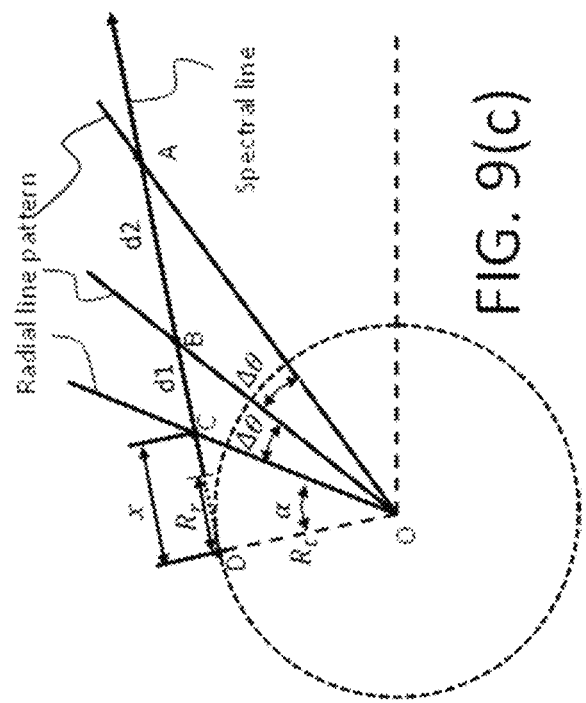
FIGS. 9(a) to 9(c) show at least one embodiment of a reference radial line pattern (FIG. 9(a)), a simulated distorted image in polar coordinate with $R_r>0$ and $R_t>0$ (FIG. 9(b)), and the coordinate of the scanning spectral line relative to the radial line pattern (FIG. 9(c)) for at least one embodiment of a method for determining $R_t$ by imaging radial lines of a target plane in accordance with one or more aspects of the present disclosure in accordance with one or more aspects of the present disclosure.
Figure 9B:
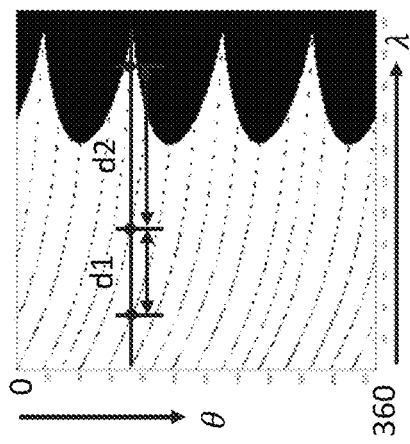
Figure 9A:
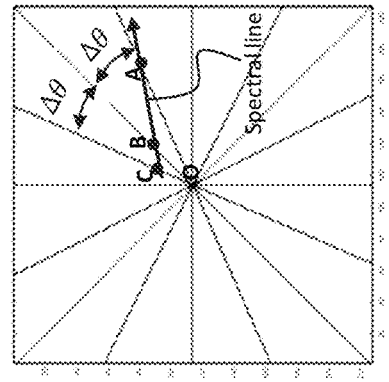

The magnitude of the tangential shift $|R_t|$ can also be determined by imaging at least three (3) equally spaced radial lines in a polar coordinate. FIG. 9 shows the method of solving $R_t$ by imaging at least 3 angularly equally spaced radial lines. As shown in FIG. 9(a), three radial lines equally spaced with an angle $\Delta\theta$ from each other are provided in a target plane to be imaged. Points A, B, and C are intersection of the radial line pattern with the scanning spectral line. FIG. 9(c) illustrates the coordinate of the scanning line relative to the radial line pattern of the target plane to be imaged. FIG. 9(b) shows that the lengths $d_1$ and $d_2$ between the intersections C and B and the intersections B and A, respectively, may be measured in the polar coordinate and may be solved by geometric relationship expressed in FIG. 9(c) and the following equations. As the angular distance between the radial lines $\Delta\theta$ is predetermined and the spaces $d_1$ and $d_2$ may be determined from the distorted image in the polar coordinate, the unknown parameters x, $\alpha$, and $R_t$ may be obtained by the following equations:

$$\text{For the triangle } OAD: \frac{x + d_1 + d_2}{R_t} = \tan(\alpha + 2\Delta\theta) \tag{4}$$

$$\text{For the triangle } OBD: \frac{x + d_1}{R_t} = \tan(\alpha + \Delta\theta) \tag{5}$$

$$\text{Apply sine law to the triangle } OCB: \frac{d_1}{\sin \Delta\theta} = \frac{\overline{OB}}{\sin \Delta OCB} = \frac{\overline{OB}}{\cos \alpha} \tag{6}$$

$$\text{Apply sine law on the triangle } OAB: \frac{d_2}{\sin \Delta\theta} = \frac{\overline{OB}}{\sin \Delta OAB} = \frac{\overline{OB}}{\cos(\alpha + 2\Delta\theta)} \tag{7}$$

$$\text{Solve } \alpha \text{ by Equation (6)/Equation (7): } \tan \alpha = \frac{1}{\sin 2\Delta\theta}\left(\cos 2\Delta\theta - \frac{d_1}{d_2}\right) \tag{8}$$

$$\text{Solve } R_t \text{ from } \left(\frac{1}{\text{equation (4)}} - \frac{1}{\text{equation (5)}}\right): R_t = \frac{d_2}{\tan(\alpha + 2\Delta\theta) - \tan(\alpha + \Delta\theta)} \tag{9}$$

$R_t$ may then be obtained by combining equation (8) with equation (9) to remove $\alpha$.

To measure the amplitude or magnitude of the radial shift $R_r$, a reference pattern may be imaged. For example, the reference pattern with multiple radial lines of a target plane is imaged, and the pixel location corresponding to the transition point of lines in a polar coordinate is found. As discussed above, if $R_r<0$, there is a slope transition on the lines in at least one image presented in the polar coordinate. The amplitude of $R_r$ may be determined by measuring the location (pixel index) of the slope transition point, which occurs at where the largest slope occurs, that is, the second derivative of the lines=0, as shown in FIG. 7(e) and FIG. 7(h). However, in one or more embodiments, this applies only when $R_r<0$.

In the situation that the radial shift is positive, that is, $R_r>0$, a target object with a different pattern is imaged by the SEE probe. For example, as shown in FIG. 10(a), a circular pattern with a radius of $R_0$ is imaged by the SEE probe. The tangential and radial offsets of the spectral line do not cause distortion in the circular pattern in the sense that the circular pattern remains circular. However, the location of the vertical line corresponding to the circle in the polar image changes. By measuring the change of the vertical lines, the offsets of the spectral line may be measured. Indeed, such methods of imaging concentric circle patterns and solving for $R_r$ using the parameters measured in the polar coordinate may be used. FIG. 10(b) shows the undistorted image may be presented in the polar coordinate assuming that there are no offsets (that is, $R_r=0$ and $R_t=0$) on the spectral line. $R_0$ may be measured from the target radius and its corresponding pixel index may be determined by calibration of the spectrometer. FIG. 10(c) shows the distorted image presented in the polar coordinate with unknown $R_r$ and $R_t$. As d can be measured on the line sensor and $R_t$ can be measured proposed by at least the method as shown in FIG. 9 and by at least the method as shown in FIGS. 7(e) to 7(h). $R_r$ may be solved by equation (10) as follows:

$$R_r = \sqrt{R_0^2 - R_t^2} - d \tag{10}$$

When $R_r<0$ as shown in FIG. 11(a), equation (11) may be applied to determine $R_r$:

$$R_r = d - \sqrt{R_0^2 - R_t^2} \tag{11}$$

FIG. 11(b) shows the undistorted image ($R_r=0$, $R_t=0$) in the polar coordinate, and FIG. 11(c) shows the distorted image in the polar coordinate when $R_r>0$ and $R_r<0$.

Figure 12A:
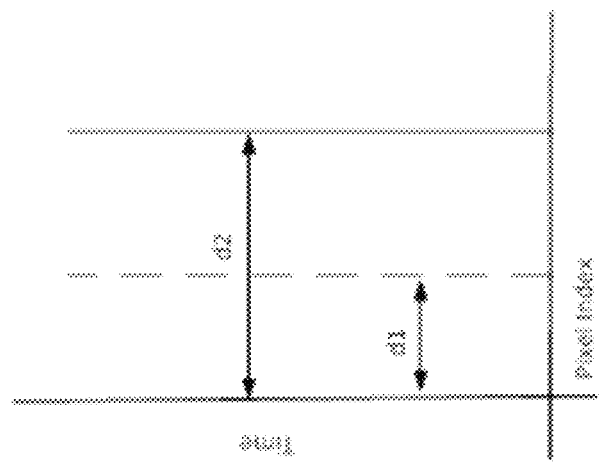
FIGS. 12(a) to 12(c) show at least one embodiment of concentric circular patterns (see FIG. 12(a) with two concentric circles having positive $R_r$ and FIG. 12(b) with two concentric circles having negative $R_r$) and a distorted image in a polar coordinate system (FIG. 12(c)) for at least one embodiment of a method for determining $R_t$ and $R_r$ by imaging a target with two circular concentric circles in accordance with one or more aspects of the present disclosure.
Figure 12B:
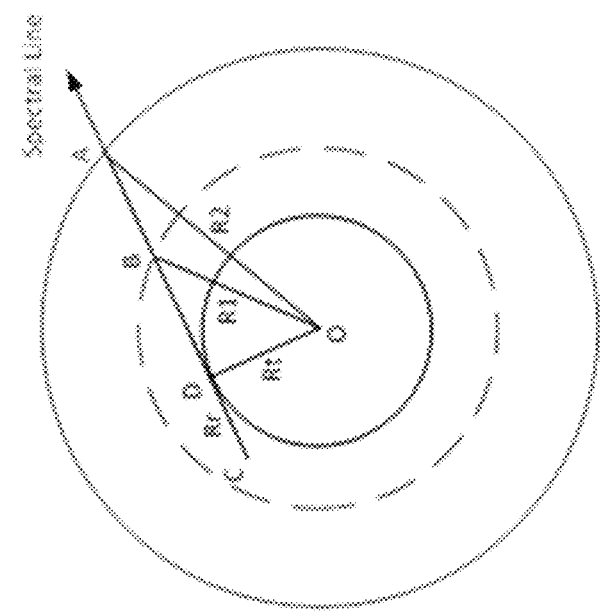

FIGS. 12(a) and 12(b) show at least one embodiment of a method for distortion correction by imaging a pattern with two concentric circles. In one or more embodiments, a pattern may be imaged with two concentric circles, and $R_t$ and $R_r$ may be solved using the parameters measured in the polar coordinate. As shown in FIG. 12(a), a pattern with two concentric circles one with a radius of $R_1$ and the other with a radius of $R_2$ is imaged by an SEE probe with positive radially shifted spectral lines. Similarly, as shown in FIG. 12(b), the pattern with two concentric circles one with the radius of $R_1$ and the other with the radius of $R_2$ is imaged by an SEE probe with negative radially shifted spectral lines. The tangential and radial offsets of the spectral line do not appear to cause distortion in the circular pattern in the sense that the circular pattern remains circular. However, the locations of the vertical lines corresponding to the two circles in the polar image change, and so do the radii of the circles in the Cartesian coordinate. By measuring the relative positions of the two vertical lines, the radial and tangential offsets of the spectral line may be measured.

Figure 12C:
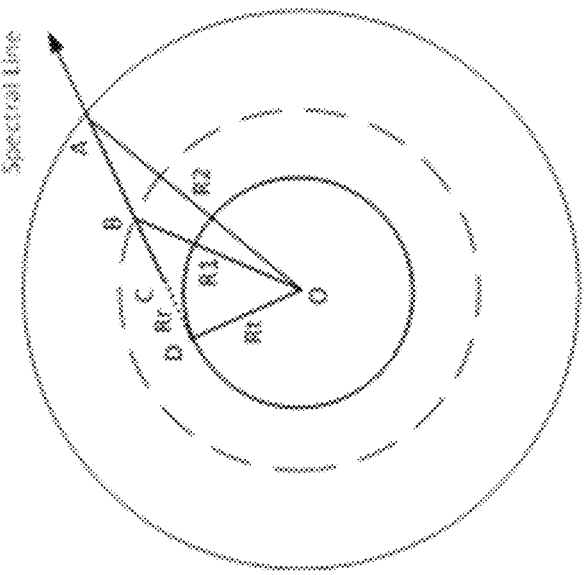

FIG. 12(c) shows the distorted image presented in the polar coordinate with unknown $R_r$ and $R_t$. As the $d_1$ and $d_2$ may be measured from the image and $R_t$ may be measured by at least the methods proposed in FIGS. 7 and 9, $R_r$ may be solved by the following equation:

Known and measured parameters: $d_1=|BC|$, $d_2=|AC|$, $R_t$ and $R_2/R_1$;
Unknown parameters: $R_r=|CD|$ ($R_r$ can be either positive or negative);
From the right triangle OAD:

$$R_t^2 + (R_r + d_2)^2 = R_2^2 \tag{12}$$

From the right triangle OBD:

$$R_t^2 + (R_r + d_1)^2 = R_1^2 \tag{13}$$

Given $R_1$ and $R_2$, both $R_r$ and $R_t$ may be solved from equation (12) and equation (13) as follows:

$$R_r = \frac{R_2^2 - R_1^2}{2(d_2 - d_1)} - \frac{d_1 + d_2}{2} \tag{14}$$

$$R_t^2 = \frac{R_2^2 + R_1^2}{2} - \frac{(R_2^2 - R_1^2)^2}{4(d_2 - d_1)^2} - \frac{(d_2 - d_1)^2}{4} \quad (15)$$

$R_r$ and $R_r$ can be solved as long as $R_1$ and $R_2$ are known for one or more embodiments. $R_1$ and $R_2$ in image space may be obtained by theoretical derivation of the SEE probe (dispersion angle v.s. wavelength), the measurement of $R_1$ and $R_2$ on the target and calibration of the spectrometer (wavelength v.s. pixel index).

In one or more embodiments, a second approach to obtain $R_1$ and $R_2$ is to use a reference SEE probe, which has known or negligible distortion, to image the circles. A third approach to obtain $R_1$ is to modify equation (15) into:

$$R_t^2 = \frac{R_1^2(k^2+1)^2}{2} - \frac{R_1^4(k^2-1)^2}{4(d_2-d_1)^2} - \frac{(d_2-d_1)^2}{4} \quad (16)$$

where $k=R_2/R_1$, the result of $R_t$ from the equation (9) is used to solve for $R_1$, and $R_2=R_1+k$, where k may always be measured from the physical target. At least the subject embodiment does not need to have extra steps to determine the sign of $R_r$. The sign of $R_t$ still needs to be determined from one or more of the aforementioned embodiments, such as the embodiment related to FIG. 6 discussed above. Both $R_r$ and $R_t$ may be solved by one-time imaging.

If only $k=R_2/R_1$ is given, that is, $R_1$ and $R_2$ are not measured directly in the image, $R_r$ may be obtained from equation 12/equation 13 as follows:

$$R_r = \frac{-(d_1 \times k^2 - d_2) \pm \sqrt{k^2 \times (d_2 - d_1)^2 - R_t^2(k^2-1)^2}}{k^2 - 1} \quad (17)$$

Equation (17) produces two solutions for $R_r$, and one of them is expected to be the invalid solution. Since equation (14) always produces the unique and valid solution, the valid solution may be found by comparing equation (17) with equation (14). If $$(d_2 - d_1)^2 \geq \frac{R_1^2(k^2-1)^2}{k^2+1} \quad (18)$$

then the valid solution from equation (17) for $R_r$ is:

$$R_r = \frac{-(d_1 \times k^2 - d_2) - \sqrt{k^2 \times (d_2 - d_1)^2 - R_t^2(k^2-1)^2}}{k^2 - 1} \quad (19)$$

and when $$(d_2 - d_1)^2 < \frac{R_1^2(k^2-1)^2}{k^2+1} \quad (20)$$

then the valid solution for $R_r$ is:

$$R_r = \frac{-(d_1 \times k^2 - d_2) + \sqrt{k^2 \times (d_2 - d_1)^2 - R_t^2(k^2-1)^2}}{k^2 - 1} \quad (21)$$

The concentric circular pattern may be designed such that either equation (18) or equation (20) is either always true within the tolerance of the spectral line offsets so that there is always only one valid solution from either equation (19) or equation (21). For example, assuming that $R_t$ is far smaller than $R_1$ ($R_t \ll R_1$), then $d_2 - d_1 \approx R_2 - R_1$. Designing the concentric circles such that $R_1 \ll R_2$ (e.g., $R_2/R_1 \approx 3$). Therefore equation (19) may be used to determine the unique valid solution. Another approach is to let a user choose either equation (19) or equation (21) based on human observation. At least one advantage of the subject embodiments is that there is no need to have extra steps to determine the signs of $R_r$.

In the one or more embodiments relating to FIGS. 10-11 and/or presented in FIG. 12, $R_r$ may be measured by using at least one circular pattern. To avoid the case that the total line shift is larger than $R_0$ (that is, $\sqrt{R_r^2 + R_t^2} > R_0$), the circular pattern does not need to be limited to just one circle. A pattern that has concentric circles with even spacing is another option. Each circle is preferably marked such that they are distinguishable in software, and/or by a processor, such as one or more of the processors discussed herein below, (such as, but not limited to, color coded, dashed, with different thickness of rings, etc.).

Figure 13:
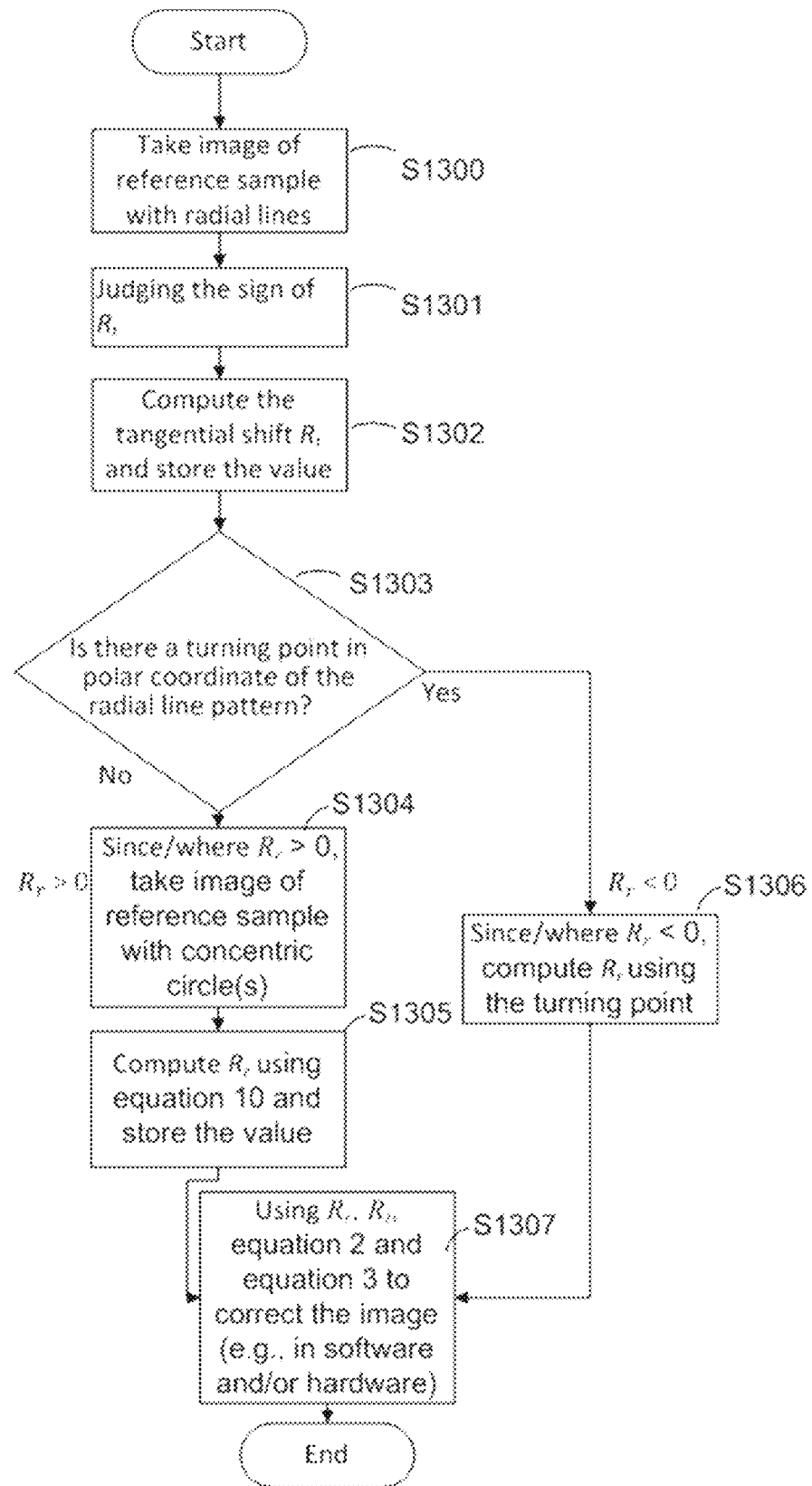
FIG. 13 is a flow chart showing at least one embodiment of a method for distortion correction by imaging a radial line pattern in accordance with one or more aspects of the present disclosure.

FIG. 13 shows a flow chart of at least one embodiment of a distortion correction/calibration method using a radial line pattern. As shown, the image of a reference sample with multiple radial lines, for example, the object as shown in FIGS. 6-9, is imaged or taken (see e.g., step S1300 in FIG. 13). The sign of the tangential shift & of the spectral line may be determined or judged (see e.g., step S1301 in FIG. 13), for example, based on a slope of a distorted image from a radial pattern in a polar coordinate. The magnitude of the tangential shift |$R_t$| is then computed based on a distorted image in a Cartesian coordinate as shown in FIG. 8(*b*) (see e.g., step S1302 in FIG. 13). Alternatively, the magnitude of the tangential shift |$R_t$| can be computed by using at least three angularly equally spaced radial lines based on equation (9) (see e.g., step S1302 in FIG. 13). The sign of the radial shift may be determined by judging whether there is a turning (transition) point in the image obtained from the reference pattern in a polar coordinate (see e.g., step S1303 in FIG. 13). In a case where the turning point exists ("Yes" in step S1303 in FIG. 13), $R_r$ is negative. The turning point can be used to compute the radial shift (see e.g., step S1306 in FIG. 13). However, in a case where the turning point does not exist ("No" in step S1303 in FIG. 13), $R_r$ is positive, and the concentric circular pattern can be imaged (see e.g., step S1304 in FIG. 13) to determine the radial shift based on equation (10) (see e.g., step S1305 in FIG. 13). As the radial shift $R_r$ and the tangential shift $R_t$ are determined, the distortion may be corrected based on equation (2) and equation (3) (see e.g., step S1307 in FIG. 13), and the image may be reconstructed without distortion.

Figure 14:
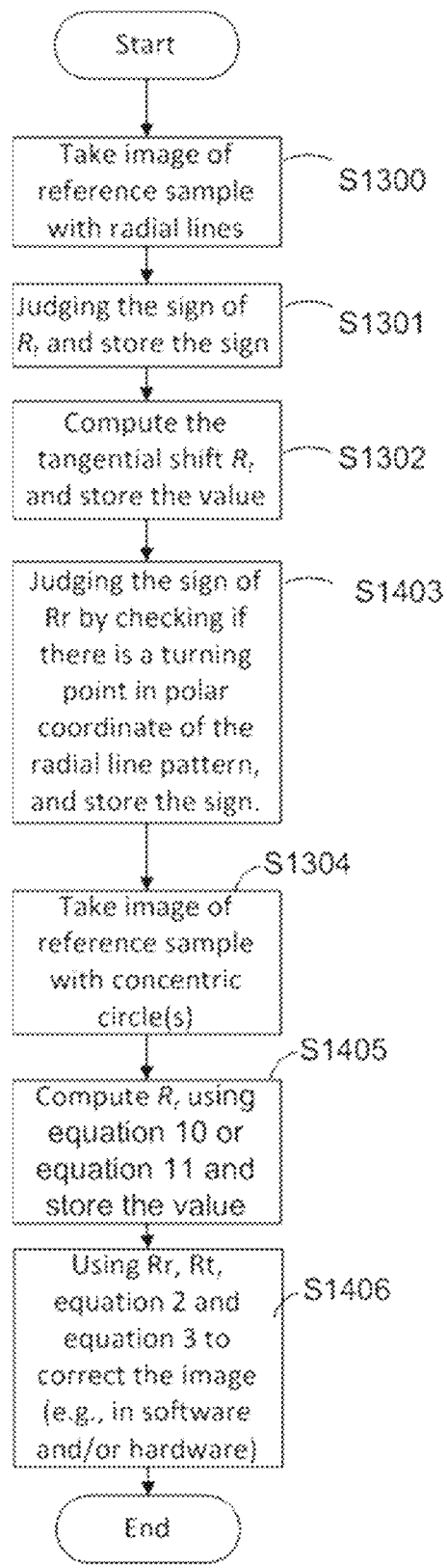
FIG. 14 is a flow chart showing at least one embodiment of a method for distortion correction by imaging both a radial line pattern and a circular pattern in accordance with one or more aspects of the present disclosure.

FIG. 14 shows a flow chart of at least another embodiment of a distortion correction/calibration method using a radial line pattern. As shown, the image of a reference sample with multiple radial lines, for example, the object as shown in FIGS. 6-9, is imaged or taken (see e.g., step S1300 in FIG. 14). The sign of the tangential shift $R_t$ of the spectral line may be determined (see e.g., step S1301 in FIG. 14) based on the slope of the distorted image from the radial pattern in a polar coordinate. The magnitude of the tangential shift $|R_t|$ is then computed (see e.g., step S1302 in FIG. 14) based on a distorted image in a Cartesian coordinate as shown in FIG. 8(b). Alternatively, the magnitude of the tangential shift $|R_t|$ may be computed by using three angularly equally spaced radial lines based on equation (9). The sign of the radial shift $R_r$ may be determined by judging whether there is a turning (transition) point in the image obtained from the reference pattern in a polar coordinate (see e.g., step S1403 in FIG. 14). In a case where the turning point exists, $R_r$ is negative. Otherwise $R_r$ is positive. An image of a reference sample with concentric circles (see e.g., step S1304 in FIG. 14) is then taken for computing & for example, based on equation (10) or equation (11) (see e.g., step S1405 in FIG. 14). As the radial shift $R_r$ and the tangential shift $R_t$ are determined, the distortion may be corrected, and the image may be reconstructed without distortion by equation (2) and equation (3) (see e.g., step S1406 in FIG. 14).

Figure 15:
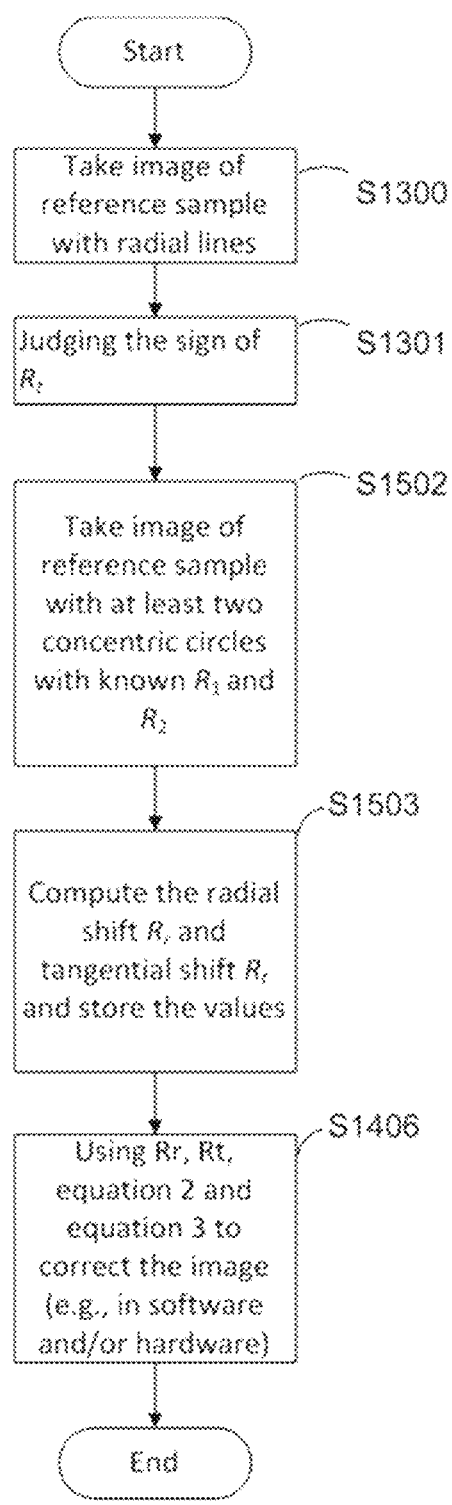
FIG. 15 is a flow chart showing at least one embodiment of a method for distortion correction by imaging a concentric circular pattern in accordance with one or more aspects of the present disclosure.

FIG. 15 shows another embodiment for distortion correction of a SEE image. Similar to the methods as shown in FIGS. 13 and 14, an image of a reference sample with multiple radial lines is taken (see e.g., step S1300 in FIG. 15). The sign of the tangential shift $R_t$ of the spectral line is determined or judged (see e.g., step S1301 in FIG. 15), for example, based on a slope of the image in a polar coordinate. An image of a reference sample with at least two concentric circles of known radius $R_1$ and $R_2$, respectively, is then taken (see e.g., step S1502 in FIG. 15). The radial shift $R_r$ and the tangential shift $R_t$ may then be calculated based on the known parameters of the concentric circles (see e.g., step S1503 in FIG. 15). The distortion may then be corrected based on $R_r$ and $R_t$ (see e.g., step S1406 in FIG. 15). In one or more embodiments of the subject method, only one pattern with two concentric circles or at least one pattern with two concentric circles may be used to determine the value of $R_r$ and $R_t$ (e.g., from equation (14) and equation (15)). The aforementioned steps for determining or identifying a sign of $R_r$ and $R_t$ as discussed above, for example in relation to FIG. 6, may be used to determine the sign of $R_r$.

Figure 16:
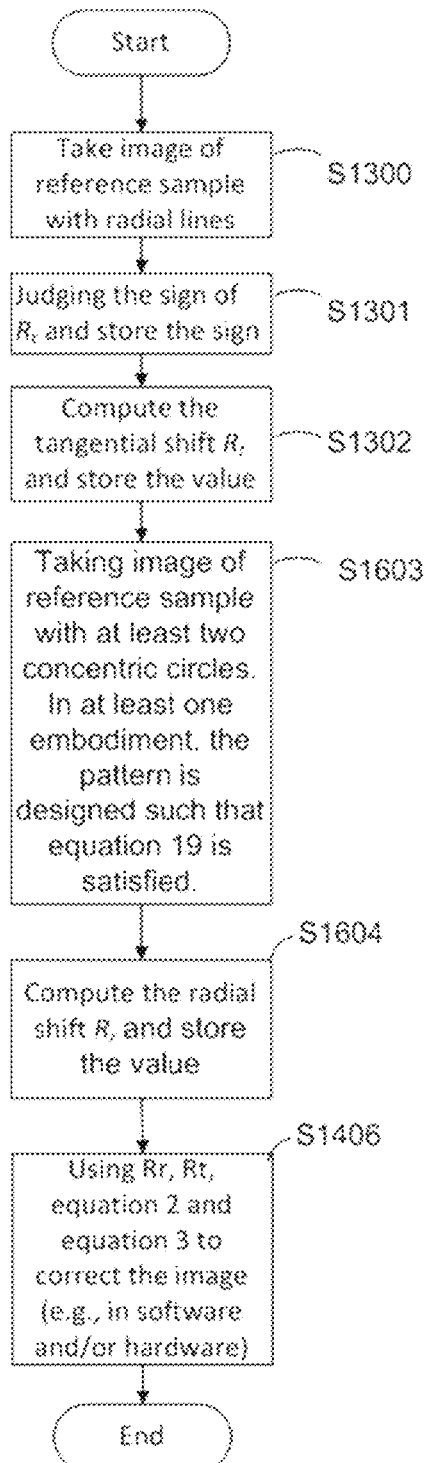
FIG. 16 is a flow chart showing at least one embodiment of another method for distortion correction in accordance with one or more aspects of the present disclosure.

In yet another embodiment, an image of a reference sample with multiple radial lines is taken (see e.g., step S1300 in FIG. 16) and processed using at least a further method for distortion correction as shown in FIG. 16. The sign of the tangential shift $R_t$ is determined (see e.g., step S1301 in FIG. 16), for example, based on the slope of the image in the polar coordinate. The tangential shift $R_t$ may then be computed (see e.g., step S1302 in FIG. 16), for example, by determining the shift of at least one of the radial lines from its original position. Alternatively, the magnitude of $R_t$ may be obtained based on three angularly equally radial lines. An image of a reference sample with at least two concentric circles is then taken (see e.g., step S1603 in FIG. 16) to then determine the radial shift $R_r$ (see e.g., step S1604 in FIG. 16). With the $R_r$ and $R_t$, the image may be corrected based by applying equation (2) and equation (3) (see e.g., step S1406 in FIG. 16; as discussed herein, the image may be corrected by one or more users using an embodiment of software, hardware or a combination thereof). $R_t$ may be solved or determined with equation (9) discussed above, and $R_r$ may be solved or determined with equation (21) above, for example, in one or more embodiments.

Figure 17:
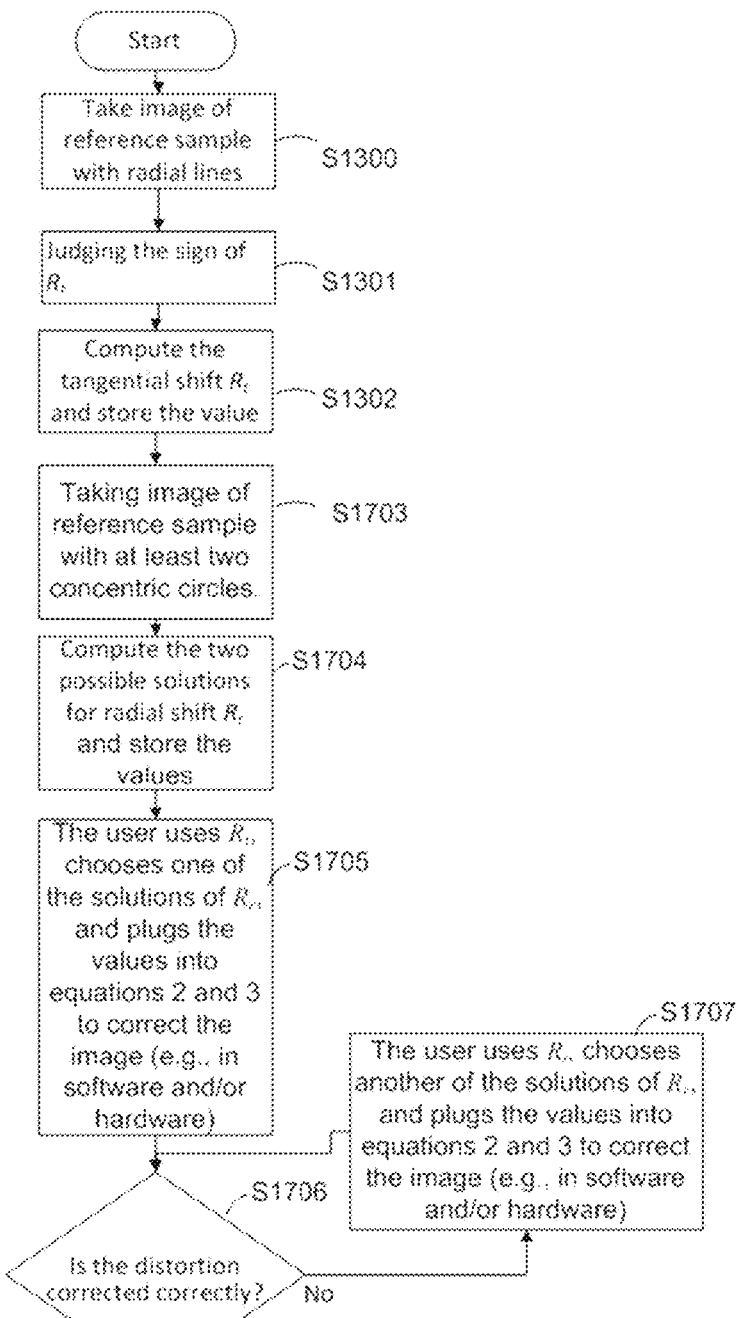
FIG. 17 is a flow chart showing at least one embodiment of another method for distortion correction in accordance with one or more aspects of the present disclosure.

FIG. 17 shows yet another embodiment of a method for distortion correction. An image of a reference sample with multiple radial lines is taken (see e.g., step S1300 in FIG. 17). The sign of the tangential shift $R_t$ is determined (see e.g., step S1301 in FIG. 17), for example, based on the slope of the image in the polar coordinate. The tangential shift $R_t$ may then be computed (see e.g., step S1302 in FIG. 17), for example, by determining the shift of at least one of the radial lines from its original position. Alternatively, the magnitude of $R_t$ may be obtained based on three angularly equally radial lines. An image of a reference sample with at least two concentric circles is then taken (see e.g., step S1703 in FIG. 17) to then determine the radial shift $R_r$ (see e.g., step S1704 in FIG. 17). $R_t$ may be solved or determined with equation (9) discussed above, for example, in one or more embodiments. In FIG. 17, two possible solutions of $R_r$ described in equation (19) and equation (21) are considered (see e.g., step S1704 in FIG. 17). One of the solutions of $R_r$ is used based on $R_t$. $R_t$ and the selected $R_r$ are used to correct the distortion based on equation (2) and equation (3) (see e.g., step S1705 in FIG. 17). However, in a case where the distortion cannot be corrected correctly or sufficiently (see determination made in step S1706 in FIG. 17), in one or more embodiments, another solution of $R_r$ may be used for performing the correction (see e.g., step S1707 in FIG. 17 when step S1706 results in "No"). In one or more embodiments, a user may decide the valid solution between the two possible solutions from equation (19) and equation (21) by looking at the correction result (see e.g., steps 1705-S1707 in FIG. 17).

The pattern may be individual or combined into one target to achieve different calibration purposes, such as color, distortion, background and white balance, etc. FIG. 18 (a) shows the combination of color with radial lines. FIG. 18 (b) shows the combination of color, radial lines and concentric circle(s). FIG. 18 (c) is similar to FIG. 18 (b) except that there is a central white area for white balance calibration purpose(s). FIG. 18 (d) and FIG. 18 (e) show the combination of radial lines with concentric circles with the same or different angular spacing. FIG. 18 (f) shows 3 sets of radial lines in which each set has different angular spacing.

One or more embodiments of the present disclosure may measure the spectral line shifts using an optical system with a 2D sensor. The optical system may magnify the spectral line shifts such that the shifts can be measured accurately. In one or more embodiments, multiple spectral lines are preferably captured to determine the center of rotation. In one or more embodiments calibration is easy to perform, and may be used for update calibration purposes even in the customer side since distortion, for example, of an SEE probe, may change with time. One or more embodiments may be used as a cross verification of the spectral line shifts measurement(s). In one or more embodiments, the measurements $R_t$ and the $R_r$ may be saved in a bar code, Quick response ("QR") code, configuration files, etc. for each individual SEE scope for distortion correction (e.g., via software and/or hardware, via software only, etc.).

While not limited to such arrangements, configurations, devices or systems, one or more embodiments of the methods discussed herein may be used with a SEE probe as aforementioned, such as, but not limited to, for example, the system 100 (see FIG. 19), the system 100' (see FIG. 20), etc. In one or more embodiments, one user may perform the method(s) discussed herein. In one or more embodiments, one or more users may perform the method(s) discussed herein.

Figure 19:
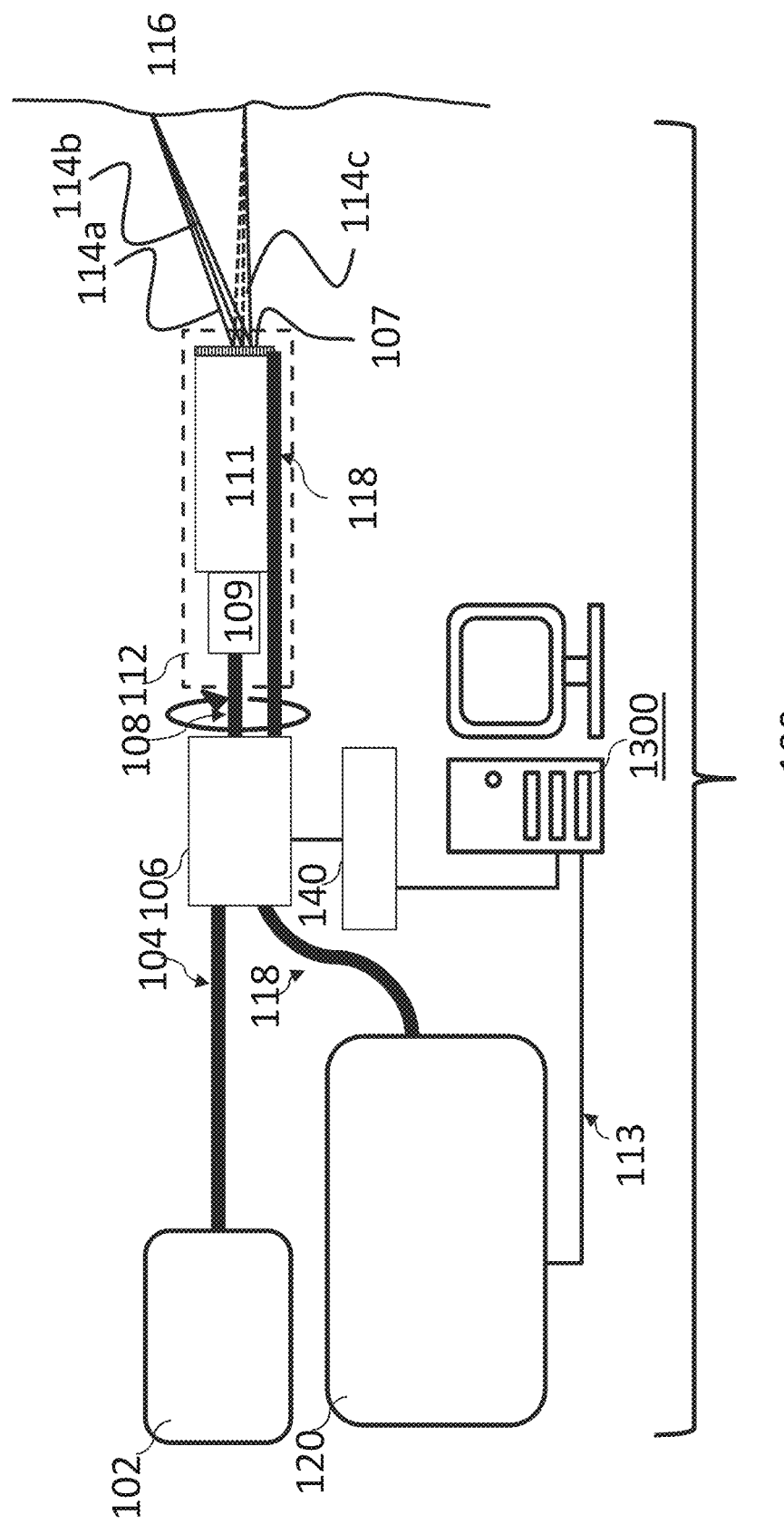
FIG. 19 is a schematic diagram of at least an embodiment of an SEE system in accordance with one or more aspects of the present disclosure.
Figure 20:
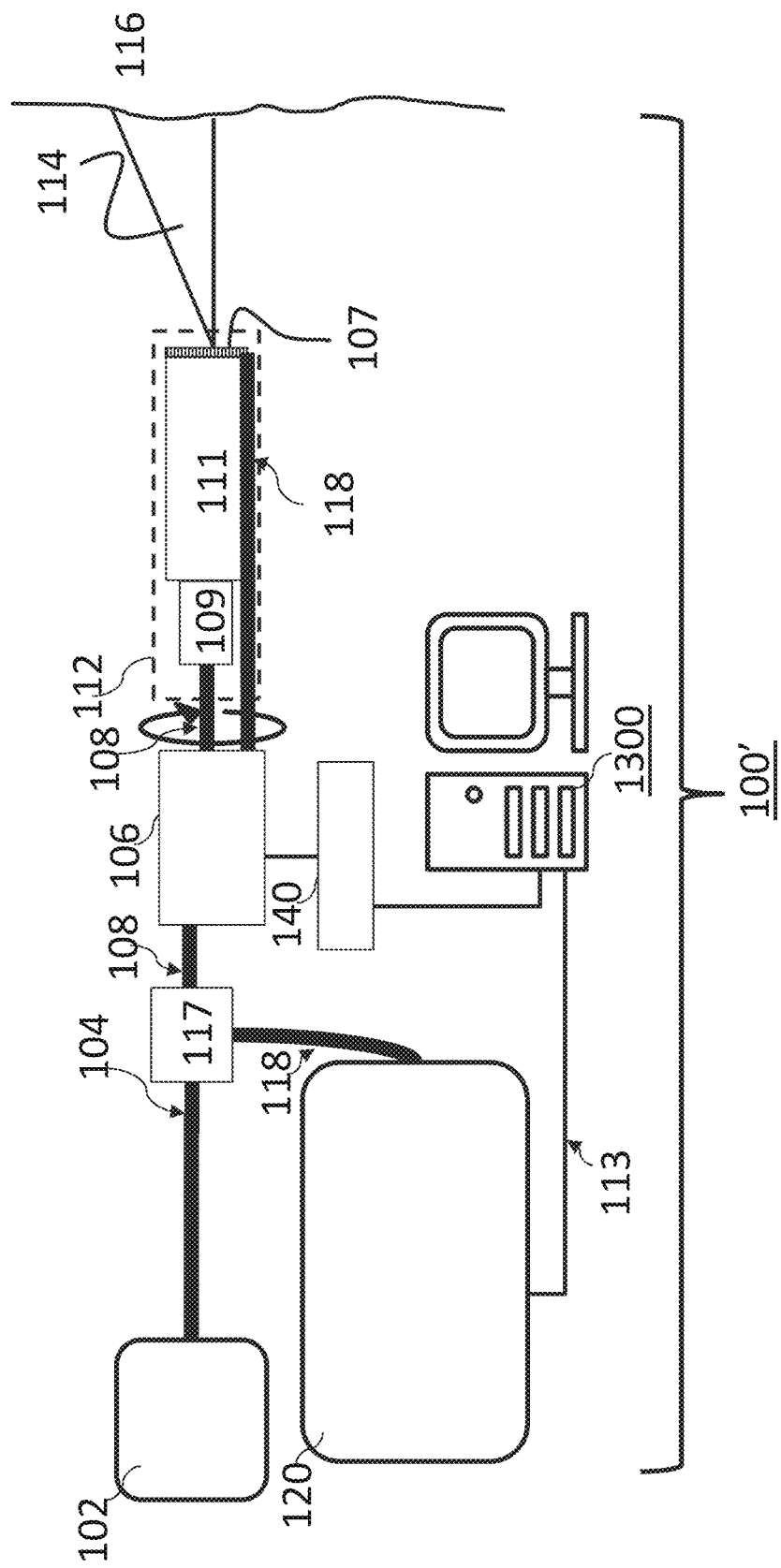
FIG. 20 is a schematic diagram of at least another embodiment of an SEE system in accordance with one or more aspects of the present disclosure.

The devices and/or systems, such as system 100, system 100', etc., may include or be connected to a broadband light source 102 (best shown in FIGS. 19-20 for systems 100', 100"). The broadband light source 102 may include a plurality of light sources or may be a single light source. The broadband light source 102 may include one or more of a laser, an organic light emitting diode (OLED), a light emitting diode (LED), a halogen lamp, an incandescent lamp, supercontinuum light source pumped by a laser, and/or a fluorescent lamp. The broadband light source 102 may be any light source that provides light which may then be dispersed to provide light which is then used to for spectral encoding of spatial information. The broadband light source 102 may be fiber coupled or may be free space coupled to the other components of the apparatus and/or system 100 or any other embodiment (including, but not limited to, system 100' (see FIG. 20), etc.) discussed herein.

As best seen in FIGS. 19-20, the system 100 and/or 100' (or any other apparatus or system discussed herein) may include a rotary junction 106. The connection between the light source 102 and the rotary junction 106 may be a free space coupling or a fiber coupling via fiber 104. The rotary junction 106 may supply just illumination light via the rotary coupling or may supply one or more of illumination light, power, and/or sensory signal lines.

The rotary junction 106 couples the light to a first waveguide 108. In at least one embodiment, the first waveguide 108 is a single mode fiber, a multimode fiber, or a polarization maintaining fiber.

The first waveguide 108 is coupled to an optical apparatus and/or system that operates as an imager or imaging device 112. The optical apparatus and/or system (or the imager) 112 may include one or more optical components, that refract, reflect, and disperse the light from the first waveguide 108 to form at least one line of illumination light 114 (e.g., additionally or alternatively, in one or more embodiments, an imaging device 112 in an apparatus or system (e.g., an SEE system) may form a plurality of illumination lines, such as, but not limited to, from three (3) wavelength ranges in the spectrum (e.g., three (3) or more illumination lines 114a, 114b, 114c, etc. may be formed such as, but not limited to, in the following colors: Red (R) (e.g., line 114a), Green (G) (e.g., line 114b), Blue (B) (e.g., line 114c), etc.), and may overlap the three illumination lines in the same or substantially the same position on an object, sample or patient 116 as best shown in FIG. 19) on a sample, an object or a patient 116 (e.g., a predetermined area in the patient, a predetermined area in and/or on a target, through the patient, through the target, etc.). In an embodiment, the line of illumination light 114 is a line connecting focal points for a wavelength range as the illumination light exits the optical apparatus and/or system (or the imager or imaging device) 112, the wavelength range being determined by the light source 102. In another embodiment, the spectrometer 120 may further limit the wavelength range by only using information from specified wavelengths of interest. In another embodiment, the line of illumination light 114 is a line formed by the illumination light as the illumination light intersects a surface of the sample, the object or the patient 116 for the range of wavelengths that are detected by the spectrometer 120. In another embodiment, the line of illumination light 114 is a line of illumination light in a wavelength range formed on a specific image plane which is determined by the detection optics. In one or more embodiments, only some of the points on the image line may be in focus while other points on the image line may not be in focus. The line of illumination light 114 may be straight or curved.

In an alternative embodiment, the optical apparatus and/or system (or the imager or imaging device) 112 may partially collimate the light from the waveguide 108 such that the light is focused onto the sample, the object or the patient 116 but the light is substantially collimated at a dispersive optical element such as a grating.

The apparatus (such as the system, 100, 100', etc.) may include a detection waveguide 118. The detection waveguide 118 may be a multimode fiber, a plurality of multimode fibers, a fiber bundle, a fiber taper, or some other waveguide. In one or more embodiments, preferably the detection waveguide 118 comprises a plurality of detection fibers (e.g., forty-five (45) fibers, sixty (60) fibers, in a range of 45-60 fibers, less than 45 fibers, more than 60 fibers, etc.). The plurality of detection fibers of the detection waveguide 118 may be spaced apart and located around the periphery (e.g., inside the periphery, around a border of the periphery, etc.) of the imaging device 112. The detection waveguide 118 gathers light from the sample, the object and/or the patient 116 which has been illuminated by light from the optical apparatus and/or system (or the imager or the imaging device) 112. The light gathered by the detection waveguide 118 may be reflected light, scattered light, and/or fluorescent light. In one embodiment, the detection waveguide 118 may be placed before or after a dispersive element of the optical apparatus and/or system 112. In one embodiment, the detection waveguide 118 may be covered by the dispersive element of the optical apparatus and/or system 112, in which case the dispersive element may act as wavelength-angular filter. In another embodiment, the detection waveguide 118 is not covered by the dispersive element of the optical apparatus and/or system, imager or imaging device 112. The detection waveguide 118 guides detection light from the sample, the object and/or the patient 116 to a spectrometer 120.

The spectrometer 120 may include one or more optical components that disperse light and guide the detection light from the detection waveguide 118 to one or more detectors. The one or more detectors may be a linear array, a charge-coupled device (CCD), a plurality of photodiodes or some other method of converting the light into an electrical signal. The spectrometer 120 may include one or more dispersive components such as a prisms, gratings, or grisms. The spectrometer 120 may include optics and opto-electronic components which allow the spectrometer 120 to measure the intensity and wavelength of the detection light from the sample, the object and/or the patient 116. The spectrometer 120 may include an analog to digital converter (ADC).

The spectrometer 120 may transmit the digital or analog signals to a processor or a computer such as, but not limited to, an image processor, a processor or computer 1300, 1300' (see e.g., FIGS. 19-20 and 22-23), a combination thereof, etc. The image processor may be a dedicated image processor or a general purpose processor that is configured to process images. In at least one embodiment, the computer 1300, 1300' may be used in place of, or in addition to, the image processor. In an alternative embodiment, the image processor may include an ADC and receive analog signals from the spectrometer 120. The image processor may include one or more of a CPU, DSP, FPGA, ASIC, or some other processing circuitry. The image processor may include memory for storing image, data, and instructions. The image processor may generate one or more images based on the information provided by the spectrometer 120. A computer or processor discussed herein, such as, but not limited to, the computer 1300, the computer 1300', the image processor, may also include one or more components further discussed herein below (see e.g., FIGS. 22-23).

One or more components of the apparatus and/or system (such as the system 100, 100', etc.) may be rotated via the rotary junction 106, or oscillated so as to scan a line of illumination light 114 so as to create a 2D array of illumination light. A 2D image may be formed by scanning a spectrally encoded line from the optical apparatus and/or system, the imager or imaging device 112 across the sample, the object and/or the patient 116. The apparatus and/or system (such as the system 100, 100', etc.) may include an additional rotary junction that couples the light from the detection fiber 118 to the spectrometer 120. Alternatively, the spectrometer 120 or a portion of the spectrometer 120 may rotate with the fiber 118. In an alternative embodiment, there is no rotary junction 106 and the light source rotates with the fiber 108. An alternative embodiment may include an optical component (mirror) after a dispersive element in the optical system or imager 112 which rotates or scans the spectrally encoded line of illumination light across the sample, the object and/or the patient 116 substantially perpendicular to the spectrally encoded line of illumination light 114 in a linear line to produce a 2D image or circumferentially in a circle so as to produce a toroidal image. Substantially, in the context of one or more embodiments of the present disclosure, means within the alignment and/or detection tolerances of the apparatus and/or system (such as the system 100, 100', etc.) and/or any other system being discussed herein. In an alternative embodiment, there is no rotary junction 106 and an illumination end of the optical apparatus and/or system or the imager 112 is scanned or oscillated in a direction perpendicular to the illumination line.

In one or more alternative embodiments, a dispersive element 107 (i.e., a diffraction grating) may be used in the optical apparatus and/or system 112 as shown, respectively, in FIGS. 19-20. In one or more embodiments (best seen in FIGS. 19 and 20), light that has been emitted from the core of the end portion of the illumination optical fiber or the first waveguide 108 may enter a spacer 111 via a refractive-index distribution lens (hereinafter referred to as "gradient index (GRIN) lens") 109. The diffraction grating 107 is formed at the tip portion of the spacer 111 as shown in FIGS. 19 and 20, and a spectral sequence 114 is formed on the subject, object or sample 116 by a light flux of white light entering the diffraction grating 107. FIG. 20 illustrates an alternative embodiment of an apparatus and/or system 100' including a spectrometer as shown in FIG. 19 (see e.g., system 100), with the exception being that a deflecting or deflected section 117 is incorporated into the system 100' of FIG. 20 such that the cable or fiber 104 and/or the cable or fiber 108 connecting the light source 102 to the rotary junction 106 and/or the optical apparatus and/or system 112 and the cable or fiber 118 connecting the spectrometer 120 to the rotary junction 106 and/or the optical apparatus and/or system or imager 112 pass through, and are connected via, the deflected section 117 (discussed further below).

In at least one embodiment, a console or computer 1300, 1300' operates to control motions of the RJ 106 via a Motion Control Unit (MCU) 140, acquires intensity data from the detector(s) in the spectrometer 120, and displays the scanned image (e.g., on a monitor or screen such as a display, screen or monitor 1309 as shown in the console or computer 1300 of any of FIGS. 19-20 and 22 and/or the console 1300' of FIG. 23 as further discussed below). In one or more embodiments, the MCU 140 operates to change a speed of a motor of the RJ 106 and/or of the RJ 106. The motor may be a stepping or a DC servo motor to control the speed and increase position accuracy. In one or more embodiments, the deflection or deflected section 117 may be at least one of: a component that operates to deflect the light from the light source to the interference optical system, and then send light received from the interference optical system towards the at least one detector; a deflection or deflected section that includes at least one of: one or more interferometers, a circulator, a beam splitter, an isolator, a coupler, a fusion fiber coupler, a partially severed mirror with holes therein, and a partially severed mirror with a tap; etc. In one or more other embodiments, the rotary junction 106 may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the SEE probe may be separate from the detection portion of the SEE probe. For example, in one or more applications, a probe may refer to the illumination assembly, which includes the illumination fiber 108 (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 118, the spectrometer 120, the computer 1300, the computer 1300', etc. The detection fibers, such as the detection fiber(s) 118, may surround the illumination fiber, such as the IF 108, and the detection fibers may or may not be covered by the grating, such as the grating 107.

In an embodiment, the first waveguide 108 may be single mode fiber. In an alternative embodiment, the first waveguide 108 may be a multimode fiber or a double clad fiber. In an embodiment, the second waveguide 118 may be a multi-mode fiber a single mode fiber, or a fiber bundle.

In an alternative embodiment, the first waveguide 108 may be an inner core of a double-clad fiber, while the second waveguide 118 may be between the inner core and the outer cladding of the double clad fiber. If a double clad fiber is used, an alternative embodiment may include an optical coupler for guiding illumination light to the inner core, and the optical coupler may also receive detection light from the outer waveguide which is then guided to the spectrometer 120.

Figure 21:
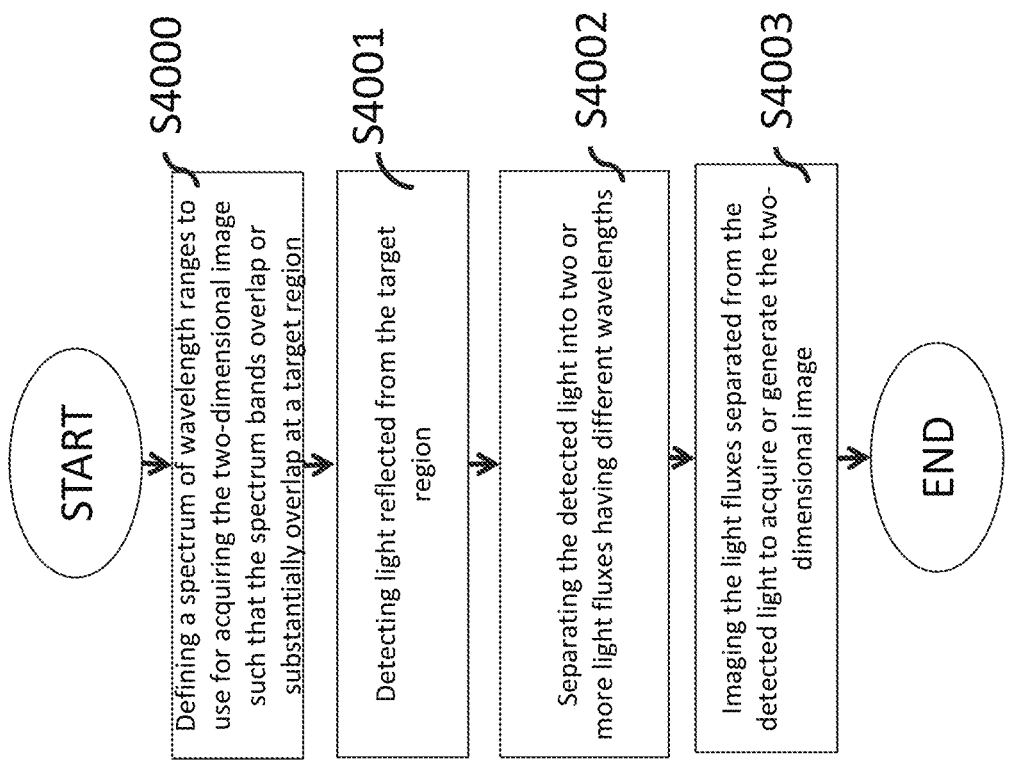
FIG. 21 is a flowchart of at least one embodiment of a method for performing SEE image in accordance with one or more aspects of the present disclosure.

In accordance with one or more aspects of the present disclosure, one or more methods for performing imaging are provided herein. FIG. 21 illustrates a flow chart of at least one embodiment of a method for performing imaging. Preferably, the method(s) may include one or more of the following: (i) defining a spectrum of wavelength ranges to use for acquiring the image such that the spectrum bands overlap or substantially overlap on a sample or target (see step S4000 in FIG. 21); (ii) detecting light reflected from the target region (see step S4001 in FIG. 21); (iii) separating the detected light into two or more light fluxes having different wavelengths (see step S4002 in FIG. 21); and (iv) imaging the light fluxes separated from the detected light to acquire or generate the black and white and/or color image (see step S4003 in FIG. 21). One or more methods may further include at least one of: using a probe grating to generate the spectrum bands that overlap or substantially overlap on the target region; and optimizing the probe grating so that a diffraction efficiency is high within the wavelength ranges. In one or more embodiments, a SEE probe may be connected to one or more systems (e.g., the system 100, the system 100', etc.) with a connection member or interface module. For example, when the connection member or interface module is a rotary junction for a SEE probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the SEE probe may be separate from the detection portion of the SEE probe. For example, in one or more applications, a probe may refer to the illumination assembly, which includes the illumination fiber 108 (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 118, the spectrometer 120, the computer 1300, the computer 1300', etc. The detection fibers, such as the detection fiber(s) 118, may surround the illumination fiber, such as the IF 108, and the detection fibers may or may not be covered by the grating, such as the grating 107.

Unless otherwise discussed herein, like numerals indicate like elements. For example, while variations or differences exist between the systems, such as, but not limited to, the system 100, the system 100', etc., one or more features thereof may be the same or similar to each other, such as, but not limited to, the light source 102 or other component(s) thereof (e.g., the console 1300, the console 1300', the RJ 106, etc.). Those skilled in the art will appreciate that the light source 102, the RJ 106, the MCU 140, the spectrometer 120 (one or more components thereof) and/or one or more other elements of the system 100, may operate in the same or similar fashion to those like-numbered elements of one or more other systems, such as, but not limited to, the system 100', etc. as discussed herein. Those skilled in the art will appreciate that alternative embodiments of the system 100, the system 100', etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100, the system 100', and the other system(s) as discussed herein, there are similarities. Likewise, while the console or computer 1300 may be used in one or more systems (e.g., the system 100, the system 100', etc.), one or more other consoles or computers, such as the console or computer 1300', etc., may be used additionally or alternatively.

Light emitted by a white light source may be transmitted by an illumination light transmission fiber and may be incident on a probe portion via the RJ 106. Additionally or alternatively, the light emitted by the white light source may be transmitted by the illumination light transmission fiber and may be incident on the probe portion (e.g., the optical apparatus and/or system or the imager 112) via a deflecting or deflected section 117 and via the RJ 106. Reflected light from the spectral sequence (e.g., light from the spectral sequence that is formed on, and is reflected by, the subject or sample; light that is reflected by the subject or sample; etc.) is taken in by a detection fiber or cable, such as the cable or fiber 118. Although one detection fiber may be used in one or more embodiments, a plurality of detection fibers may be used additionally or alternatively. In one or more embodiments, the detection fiber may extend to and/or near the end of the probe section. For example, the detection fiber 118 may have a detection fiber portion (e.g., a fiber extending through the probe portion) that extends from or through the RJ 106 through, and to and/or near (e.g., adjacent to the end of the probe section, about the end of the probe portion, near the end of the probe portion closest to the sample, etc.) the end of, the probe section (e.g., the optical apparatus and/or system 112). The light taken in by the detection fiber 118 is separated into spectral components and detected by at least one detector, such as, but not limited to, a spectrometer 120 (and/or one or more components thereof as discussed herein), provided at the exit side of the detection fiber 118. In one or more embodiments, the end of the detection fiber 118 that takes in the reflected light may be disposed on or located near at least one of: the diffraction grating 107, the end of the spacer 111, the end of the probe portion or the imager 112, etc. Additionally or alternatively, the reflected light may be passed at least one of: through the probe portion, through the GRIN lens, through the rotary junction, etc., and the reflected light may be passed, via a deflecting or deflected section 117 (discussed above and below), to the spectrometer 120. As the portion extending from the RJ 106 to the probe portion 112 is rotated about the rotational axis extending in the longitudinal direction of the probe portion 112, the spectral sequence moves in a direction orthogonal to the spectral sequence, and reflectance information in two-dimensional directions may be obtained. Arraying these pieces (e.g., the reflectance information in two-dimensional directions) of information makes it possible to obtain a two-dimensional image.

Preferably, in one or more embodiments including the deflecting or deflected section 117, the deflected section 117 operates to deflect the light from the light source 102 to the probe portion (e.g., element or the imager 112), and then send light received from the probe portion towards at least one detector (e.g., the spectrometer 120, one or more components of the spectrometer 120, etc.). In one or more embodiments, the deflected section 117 may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system or of the system, such as, but not limited to, one or more of the light source 102, the deflected section 117, the rotary junction 106, and/or the probe portion (e.g., element 112) (and/or one or more components thereof).

There are many ways to compute intensity, viscosity, resolution (including increasing resolution of one or more images), creation of black and white and/or color images or any other measurement discussed herein, digital as well as analog. In at least one embodiment, a computer, such as the console or computer 1300, 1300', may be dedicated to control and monitor the SEE devices, systems, methods and/or storage mediums described herein.

The electric signals used for imaging and/or performing one or more of the methods discussed herein may be sent to one or more processors, such as, but not limited to, a computer 1300 (see e.g., FIGS. 19-20 and 22), a computer 1300' (see e.g., FIG. 23), etc. as discussed further below, via cable(s) or wire(s), such as, but not limited to, the cable(s) or wire(s) 113 (see FIGS. 19-20 and 22).

Figure 22:
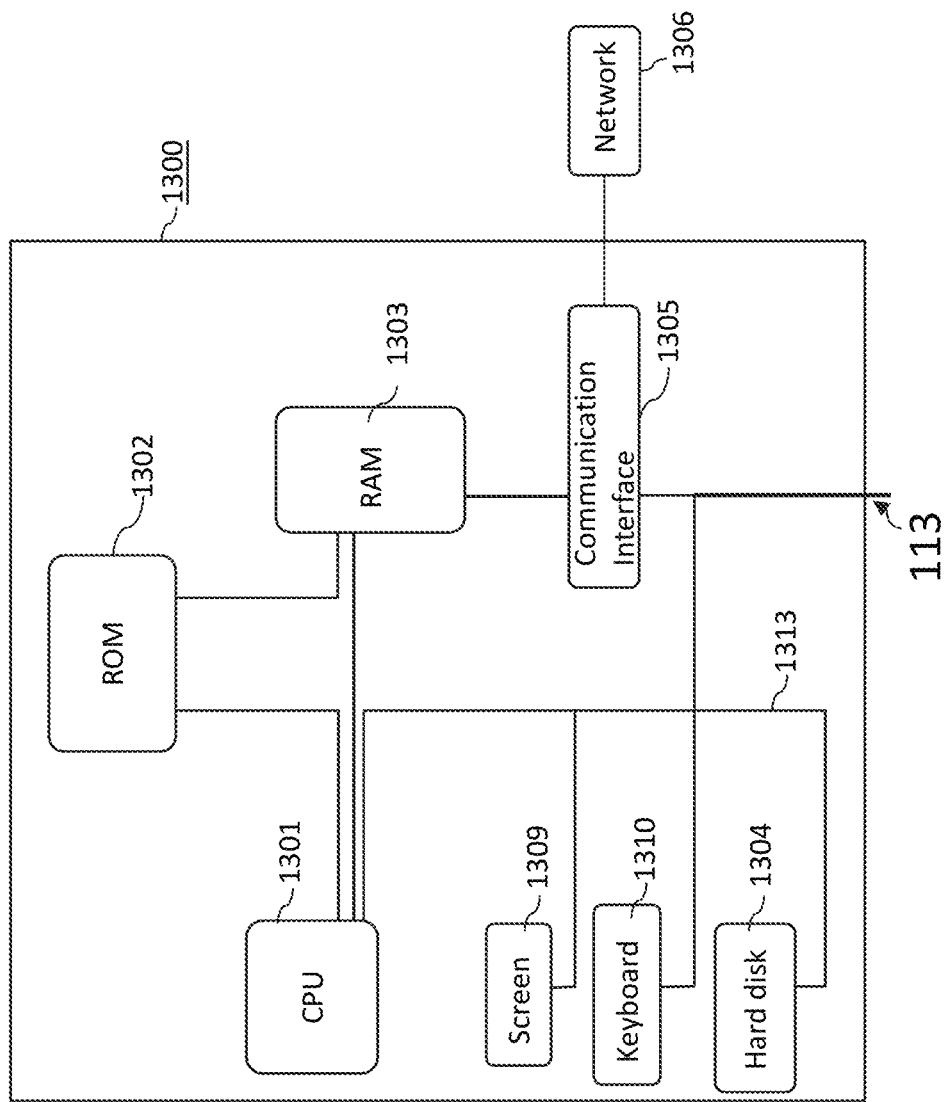
FIG. 22 shows a schematic diagram of an embodiment of a computer that may be used with one or more embodiments of an apparatus or system or one or more methods discussed herein in accordance with one or more aspects of the present disclosure.

Various components of a computer system 1300 (see e.g., the console or computer 1300 as shown in FIGS. 19-20) are provided in FIG. 22. A computer system 1300 may include a central processing unit ("CPU") 1301, a ROM 1302, a RAM 1303, a communication interface 1305, a hard disk (and/or other storage device) 1304, a screen (or monitor interface) 1309, a keyboard (or input interface; may also include a mouse or other input device in addition to the keyboard) 1310 and a BUS or other connection lines (e.g., connection line 1313) between one or more of the aforementioned components (e.g., including but not limited to, being connected to the console, the probe, any motor discussed herein, a light source, etc.). In addition, the computer system 1300 may comprise one or more of the aforementioned components. For example, a computer system 1300 may include a CPU 1301, a RAM 1303, an input/output (I/O) interface (such as the communication interface 1305) and a bus (which may include one or more lines 1313 as a communication system between components of the computer system 1300; in one or more embodiments, the computer system 1300 and at least the CPU 1301 thereof may communicate with the one or more aforementioned components of a device or system, such as, but not limited to, a system using a motor, a rotary junction, etc.), and one or more other computer systems 1300 may include one or more combinations of the other aforementioned components (e.g., the one or more lines 1313 of the computer 1300 may connect to other components via line 113). The CPU 1301 is configured to read and perform computer-executable instructions stored in a storage medium. The computer-executable instructions may include those for the performance of the methods and/or calculations described herein. The system 1300 may include one or more additional processors in addition to CPU 1301, and such processors, including the CPU 1301, may be used for tissue or sample characterization, diagnosis, evaluation, treatment and/or imaging (and/or any other process discussed herein). The system 1300 may further include one or more processors connected via a network connection (e.g., via network 1306). The CPU 1301 and any additional processor being used by the system 1300 may be located in the same telecom network or in different telecom networks (e.g., performing technique(s) discussed herein may be controlled remotely).

Figure 23:
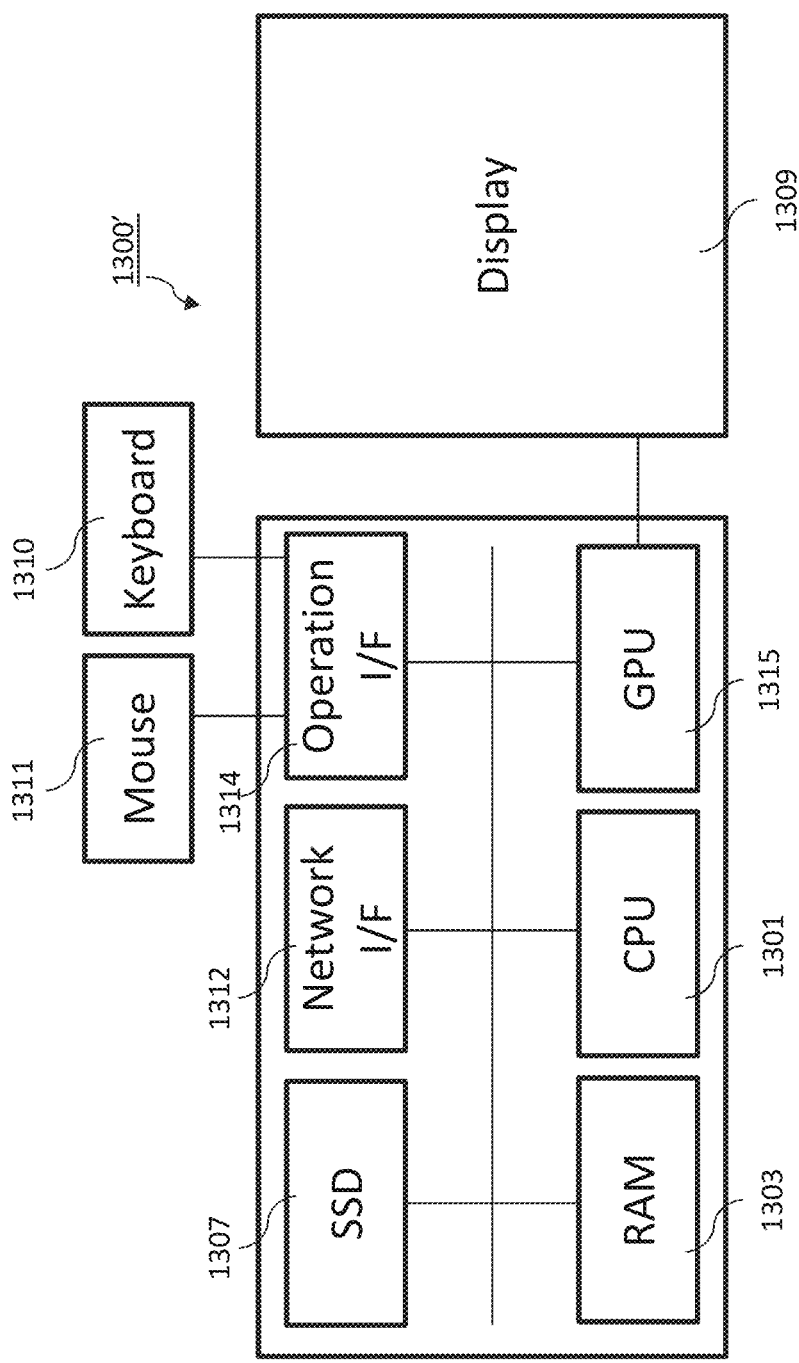
FIG. 23 shows a schematic diagram of another embodiment of a computer that may be used with one or more embodiments of an apparatus or system or methods discussed herein in accordance with one or more aspects of the present disclosure.

The I/O or communication interface 1305 provides communication interfaces to input and output devices, which may include a light source, a spectrometer, an SEE probe, an apparatus and/or system (e.g., the system 100, the system 100', etc.), the communication interface of the computer 1300 may connect to other components discussed herein via line 113 (as diagrammatically shown in FIG. 22), a microphone, a communication cable and a network (either wired or wireless), a keyboard 1310, a mouse (see e.g., the mouse 1311 as shown in FIG. 23), a touch screen or screen 1309, a light pen and so on. The Monitor interface or screen 1309 provides communication interfaces thereto.

Any methods and/or data of the present disclosure, such as the methods for performing tissue or sample characterization, diagnosis, examination, treatment and/or imaging (including, but not limited to, increasing image resolution, distortion measurement and correction, etc.) and/or any other process as discussed herein, may be stored on a computer-readable storage medium. A computer-readable and/or writable storage medium used commonly, such as, but not limited to, one or more of a hard disk (e.g., the hard disk 1304, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1303), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1307 in FIG. 23), SRAM, etc.), an optional combination thereof, a server/database, etc. may be used to cause a processor, such as, the processor or CPU 1301 of the aforementioned computer system 1300 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1300, etc., as described above may be achieved utilizing suitable hardware, such as that illustrated in the figures. Functionality of one or more aspects of the present disclosure may be achieved utilizing suitable hardware, such as that illustrated in FIG. 22. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1301 (as shown in FIG. 22) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1300' is shown in FIG. 23. The computer 1300' includes a central processing unit (CPU) 1301, a graphical processing unit (GPU) 1315, a random access memory (RAM) 1303, a network interface device 1312, an operation interface 1314 such as a universal serial bus (USB) and a memory such as a hard disk drive or a solid state drive (SSD) 1307. Preferably, the computer or console 1300' includes a display 1309. The computer 1300' may connect with a motor, a console, and/or any other component of the device(s) or system(s) discussed herein via the operation interface 1314 or the network interface 1312 (e.g., via a cable or fiber, such as the cable or fiber 113 as similarly shown in FIG. 22). A computer, such as the computer 1300', may include a motor or motion control unit (MCU) in one or more embodiments. The operation interface 1314 is connected with an operation unit such as a mouse device 1311, a keyboard 1310 or a touch panel device. The computer 1300' may include two or more of each component.

At least one computer program is stored in the SSD 1307, and the CPU 1301 loads the at least one program onto the RAM 1303, and executes the instructions in the at least one program to perform one or more processes described herein, as well as the basic input, output, calculation, memory writing and memory reading processes.

The computer, such as the computer 1300, 1300', may communicate with an MCU, a rotary junction, a needle, etc. to perform imaging, diagnosis, treatment and/or any other process discussed herein, and reconstructs an image from the acquired intensity data (and may perform distortion measurement and correction as aforementioned). The monitor or display 1309 displays the reconstructed image, and may display other information about the imaging condition or about an object to be imaged. The monitor 1309 also provides a graphical user interface for a user to operate any system discussed herein. An operation signal is input from the operation unit (e.g., such as, but not limited to, a mouse device 1311, a keyboard 1310, a touch panel device, etc.) into the operation interface 1314 in the computer 1300', and corresponding to the operation signal the computer 1300' instructs any system discussed herein to set or change the imaging condition (e.g., improving resolution of an image or images), and to start or end the imaging. A light or laser source and a spectrometer and/or detector may have interfaces to communicate with the computers 1300, 1300' to send and receive the status information and the control signals. One or more embodiments may be employed via software and/or hardware.

The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, any of the other storage mediums discussed herein, etc.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 8,045,177; 8,145,018; 8,838,213; 9,254,089; 9,295,391; 9,415,550; and 9,557,154 and arrangements and methods of facilitating photoluminescence imaging, such as those disclosed in U.S. Pat. No. 7,889,348 to Tearney et al. Other exemplary SEE systems are described, for example, in U.S. Pat. Pubs. 2016/0341951, 2016/0349417, 2017/0035281, 2017/167861, 2017/0168232, 2017/0176736, 2017/0290492, 2017/0322079, 2012/0101374 and 2018/0017778; and WO2015/116951; WO2015/116939; WO2017/117203; WO2017/024145; WO2017/165511; and WO2017/139657, each of which patents, patent publications and patent application(s) are incorporated by reference herein in their entireties. As aforementioned, other imaging techniques may be alternatively or additionally used with the apparatuses, systems, methods and storage mediums discussed herein.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A method for correcting distortion of a spectrally encoded endoscopy (SEE) image, comprising:
   scanning a first reference pattern comprising a plurality of radial lines with an SEE spectral line to obtain a first image;
   determining a sign of a tangential shift of the spectral line based on a slope of at least one of the radial lines of the first image in a polar coordinate;
   computing a magnitude of the tangential shift based on at least one of the radial lines of the first image in either a polar coordinate or a Cartesian coordinate;
   determining a sign of a radial shift of the spectral line based on whether the slope has a turning point or not;
   in a case where the radial shift is determined to be negative, either computing a magnitude of the radial shift by measuring a location of the turning point, or scanning a second reference pattern comprising at least a circle with the SEE spectral line to obtain a second image and computing the magnitude of the radial shift based on the magnitude of the tangential shift, a radius of the circle, and a position or distance d of or along the SEE spectral line where d is measured using a line sensor, is measured from the distorted SEE image, and/or is corresponding to the circle;
   in a case where the radial shift is determined to be positive, scanning the second reference pattern comprising at least the circle with the SEE spectral line to obtain the second image and computing the magnitude of the radial shift based on the magnitude of the tangential shift, a radius of the circle, and a position or distance d of or along the SEE spectral line where d is measured using a line sensor, is measured from the distorted SEE image, and/or is corresponding to the circle; and
   applying the tangential shift and the radial shift for correcting the distortion of the SEE image.

2. The method according to claim 1, wherein the step of computing the magnitude of the tangential shift comprises determining a shift of the radial line of the first image from an original position in the Cartesian coordinate.

3. The method according to claim 1, wherein the step of computing the magnitude of the tangential shift comprises:
- selecting at least three radial lines that are equally spaced from each other with an angle and each intersecting with the spectral line at an intersection point; and
- computing the magnitude of the tangential shift based on the angle, a first distance between the intersecting points of a first and a second of the at least three radial lines, and a second distance between the intersecting points of the second and a third of the intersecting points.

4. The method according to claim 1, wherein the step of computing a magnitude of the radial shift further comprises measuring the location of the turning point by determining where a second derivative of the radial line is zero in a case where the radial shift is determined to be negative and where the location of the turning point is measured.

5. The method according to claim 1, wherein when the sign of the radial shift is positive, the magnitude of the radial shift is computed by the following equation:

$$R_r = \sqrt{R_0^2 - R_t^2} - d,$$

where $R_r$ is the radial shift, $R_t$ is the tangential shift, $R_0$ is the radius of the circle, and d is the position or distance of or along the SEE spectral line that is measured using the line sensor, that is measured from the distorted SEE image, and/or that is corresponding to the circle.

6. The method according to claim 1, wherein when the sign of the radial shift is negative and where the magnitude of the radial shift is computed based on the magnitude of the tangential shift, the radius of the circle, and the position or distance d, the magnitude of the radial shift is computed by the following equation:

$$R_r = d - \sqrt{R_0^2 - R_t^2},$$

where $R_r$ is the radial shift, $R_t$ is the tangential shift, $R_0$ is the radius of the circle, and d is the position or distance of or along the SEE spectral line that is measured using the line sensor, that is measured from the distorted SEE image, and/or that is corresponding to the circle.

7. The method according to claim 1, wherein the step of applying the tangential shift and the radial shift for correcting the distortion of the SEE image further comprises applying the tangential shift and the radial shift to determine an actual location (x', y') of the radial lines represented by:

$$x' = \rho \cos\theta - R_t \sin\theta + R_r \cos\theta; \text{ and}$$

$$y' = \rho \sin\theta + R_t \cos\theta + R_r \sin\theta,$$

where $\rho$ is pixel index along the SEE spectral line, and $\theta$ is rotation angle of the SEE spectral line.

8. A method for correcting distortion of a spectrally encoded endoscopy (SEE) image, comprising:
- scanning a first reference pattern comprising a plurality of radial lines with an SEE spectral line to obtain a first image;
- determining a sign of a tangential shift of the spectral line based on a slope of at least one of the radial lines of the first image in a polar coordinate;
- scanning a second reference pattern comprising at least two concentric circles with the SEE spectral line to obtain a second image, the two concentric circles having a first radius and a second radius, respectively;
- computing the tangential shift and a radial shift of the SEE spectral line by measuring locations of the spectral line corresponding to the two concentric circles in the polar coordinate; and
- applying the tangential shift and the radial shift for correcting the distortion of the SEE image.

9. The method according to claim 8, wherein the step of computing the tangential shift comprises determining a shift of the radial line of the first image from an original position in the Cartesian coordinate.

10. The method according to claim 8, wherein the radial shift is calculated based on the following equation:

$$R_r = \frac{R_2^2 - R_1^2}{2(d_2 - d_1)} - \frac{d_1 + d_2}{2}$$

where $R_1$ is the first radius and $R_2$ is the second radius, and $d_1$ and $d_2$ are measured from the distorted image in the polar coordinate.

11. The method according to claim 8, wherein the tangential shift is calculated based on the following equation:

$$R_t^2 = \frac{R_2^2 + R_1^2}{2} - \frac{(R_2^2 - R_1^2)^2}{4(d_2 - d_1)^2} - \frac{(d_2 - d_1)^2}{4}$$

where $R_1$ is the first radius and $R_2$ is the second radius, and $d_1$ and $d_2$ are measured from the distorted image in the polar coordinate.

12. The method according to claim 8, wherein the step of applying the tangential shift and the radial shift for correcting the distortion of the SEE image further comprises applying the tangential shift and the radial shift to determine an actual location (x', y) of the radial lines represented by:

$$x' = \rho \cos\theta - R_t \sin\theta + R_r \cos\theta; \text{ and}$$

$$y' = \rho \sin\theta + R_t \cos\theta + R_r \sin\theta,$$

where $\rho$ is pixel index along the SEE spectral line, and $\theta$ is rotation angle of the SEE spectral line.

13. A method for correcting distortion of a spectrally encoded endoscopy (SEE) image, comprising:
- scanning a first reference pattern comprising a plurality of radial lines with an SEE spectral line to obtain a first image;
- determining a sign of a tangential shift of the spectral line based on a slope of at least one of the radial lines of the first image in a polar coordinate;
- determining a magnitude of the tangential shift based on a shift of at least one of the plurality of the radial lines on a Cartesian coordinate or based on at least three angularly equally spaced radial lines included in the plurality of radial lines scanned by the SEE spectral line;
- scanning a second reference pattern comprising at least two concentric circles with the SEE spectral line to obtain a second image, the two concentric circles having a first radius and a second radius, respectively;
- providing a ratio of the second radius to the first radius;
- computing a radial shift of the spectral lines based on the tangential shift, the ratio, and positions or distances of or along the SEE spectral line measured using a line sensor, measured from the distorted SEE image, and/or corresponding to the at least two concentric circles; and applying the tangential shift and the radial shift for correcting the distortion of the SEE image.

14. The method according to claim 13, wherein the step of computing the magnitude of the tangential shift comprises determining a shift of the radial line of the first image from an original position in the Cartesian coordinate.

15. The method according to claim 13, wherein the step of computing the magnitude of the tangential shift comprises:

selecting at least three radial lines that are equally spaced from each other with an angle and each intersecting with the spectral line at an intersection point; and computing the magnitude of the tangential shift based on the angle, a first distance between the intersecting points of a first and a second of the at least three radial lines, and a second distance between the intersecting points of the second and a third of the intersecting points.

16. The method according to claim 13, wherein the radial shift is calculated based on the following first equation:

$$R_r = \frac{-(d_1 \times k^2 - d_2) \pm \sqrt{k^2 \times (d_2 - d_1)^2 - R_t^2(k^2 - 1)^2}}{k^2 - 1},$$

where k is the ratio of the second radius to the first radius, and $d_1$ and $d_2$ are measured from the distorted image in the polar coordinate, and wherein the two possible values of the first equation are compared to the following second equation:

$$R_r = \frac{R_2^2 - R_1^2}{2(d_2 - d_1)} - \frac{d_1 + d_2}{2},$$

such that: (i) where the following equation is met:

$$(d_2 - d_1)^2 \geq \frac{R_1^2(k^2 - 1)^2}{k^2 + 1},$$

then the following value for the radial shift is used:

$$R_r = \frac{-(d_1 \times k^2 - d_2) - \sqrt{k^2 \times (d_2 - d_1)^2 - R_t^2(k^2 - 1)^2}}{k^2 - 1},$$

or (ii) where the following equation is met:

$$(d_2 - d_1)^2 < \frac{R_1^2(k^2 - 1)^2}{k^2 + 1},$$

then the following value for the radial shift is used:

$$R_r = \frac{-(d_1 \times k^2 - d_2) + \sqrt{k^2 \times (d_2 - d_1)^2 - R_t^2(k^2 - 1)^2}}{k^2 - 1}.$$

17. The method according to claim 13, wherein the step of applying the tangential shift and the radial shift for correcting the distortion of the SEE image further comprises applying the tangential shift and the radial shift to determine an actual location (x', y') of the radial lines represented by:

x'=ρ cos θ−$R_t$ sin θ+$R_r$ cos θ; and y'=ρ sin θ+$R_t$ cos θ+$R_r$ sin θ, where ρ is pixel index along the SEE spectral line, and θ is rotation angle of the SEE spectral line.

18. A method for correcting distortion of a spectrally encoded endoscopy (SEE) image, comprising:

scanning a first reference pattern comprising a plurality of radial lines with an SEE spectral line to obtain a first image;

determining a sign of a tangential shift of the spectral line based on a slope of at least one of the radial lines of the first image in a polar coordinate;

determining a magnitude of the tangential shift based on a shift of at least one of the plurality of the radial lines on a Cartesian coordinate or based on at least three angularly equally radial lines included in the plurality of radial lines scanned by the SEE spectral line;

scanning a second reference pattern comprising at least two concentric circles with the SEE spectral line to obtain a second image, the two concentric circles having a first radius and a second radius, respectively;

providing a ratio of the second radius to the first radius;

computing two possible values of a radial shift of the spectral lines based on the tangential shift, the ratio, and positions or distances of or along the SEE spectral line measured using a line sensor, measured from the distorted SEE image, and/or corresponding to the at least two concentric circles;

selecting a first possible value of the two possible values of the radial shift;

applying the tangential shift and the selected first possible value of the radial shift for correcting the distortion of the SEE image; and selecting the other of the two possible values of the radial shift to correct the distortion in a case where the distortion is not corrected by the first possible value.

* * * * *